(12) United States Patent
Kadow et al.

(10) Patent No.: US 6,362,217 B2
(45) Date of Patent: Mar. 26, 2002

(54) TAXANE ANTICANCER AGENTS

(75) Inventors: John F. Kadow, Wallingford; Wendy S. Schwartz, Windsor; Paul M. Scola; Qiufen May Xue, both of Glastonbury; Mark D. Wittman, Wallingford, all of CT (US); Mu-Jen Wu, Albertson, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/802,264

(22) Filed: Mar. 8, 2001

Related U.S. Application Data

(60) Provisional application No. 60/190,174, filed on Mar. 17, 2000.

(51) Int. Cl.$^7$ ........................ A61K 31/35; C07D 305/14
(52) U.S. Cl. ........................ 514/449; 549/510; 549/511
(58) Field of Search .................... 514/449; 549/510, 549/511

(56) References Cited

U.S. PATENT DOCUMENTS

| | | | |
|---|---|---|---|
| 4,814,470 A | 3/1989 | Colin et al. | |
| 4,960,790 A | 10/1990 | Stella et al. | |
| 5,271,268 A | 12/1993 | Ikeuchi et al. | |
| 5,283,253 A | 2/1994 | Holton et al. | |
| 5,336,785 A | 8/1994 | Holton | |
| 5,478,854 A | 12/1995 | Farina et al. | |
| 5,773,461 A | 6/1998 | Wittman et al. | |
| 5,912,264 A | 6/1999 | Wittman et al. | |
| 5,977,386 A | 11/1999 | Staab et al. | |
| 6,211,363 B1 * | 4/2001 | Terasawa et al. | 544/60 |
| 6,218,553 B1 * | 4/2001 | Ojima | 549/510 |
| 6,222,053 B1 * | 4/2001 | Zamir et al. | 549/510 |
| 6,229,207 B1 * | 5/2001 | Lui | 549/510 |
| 6,232,477 B1 * | 5/2001 | Bouchard et al. | 549/510 |
| 6,239,167 B1 * | 5/2001 | Bissery | 514/449 |
| 6,248,572 B1 * | 6/2001 | Choi et al. | 435/123 |
| 6,262,107 B1 * | 7/2001 | Li et al. | 514/449 |
| 6,262,281 B1 * | 7/2001 | Swindell et al. | 549/510 |
| 6,268,381 B1 * | 7/2001 | Shimizu et al. | 514/320 |
| 6,271,384 B1 * | 8/2001 | Nicolaou et al. | 546/281.7 |
| 6,281,368 B1 * | 8/2001 | McChesney et al. | 549/510 |
| 6,291,690 B1 * | 9/2001 | Mayhew et al. | 549/510 |
| 6,291,691 B1 * | 9/2001 | Holton et al. | 549/510 |
| 6,291,692 B1 * | 9/2001 | Holton et al. | 549/510 |

FOREIGN PATENT DOCUMENTS

| | | |
|---|---|---|
| WO | WO 94/17050 | 8/1994 |
| WO | WO 94/29288 | 12/1994 |
| WO | WO 97/15269 | 5/1997 |
| WO | WO 98/28288 | 7/1998 |
| WO | WO 98/38862 | 9/1998 |

OTHER PUBLICATIONS

G.I. Georg, et al, J. Org. Chem., 61(8), pp. 2664–2676, 1996.
M. Wright, et al, Pharmacochem Libr., 22, pp. 131–164, 1995.
A. Sparreboom et al, Cancer Chemother Pharmacol., 36(4), pp. 299–304, 1995.
B. Monsarrat, et al, Drug Metabolism and Disposition, 18(6), pp. 895–901, 1990.
H. Park, et al, J. Med. Chem., 39(14), pp. 2705–2709, 1996.
S.–H. Chen, et al, Tetrahedron Letters, 34(43), pp. 6845–6848, 1993.
R. F. Ozols, et al (editors), Seminars in Oncology (Table of Contents), 26(1, Supp. 2), 1999.
E. K. Rowinsky, et al, J. National Cancer Institute, 82(15), pp. 1247–1259, 1990.

\* cited by examiner

*Primary Examiner*—Deborah C. Lambkin
(74) *Attorney, Agent, or Firm*—Samuel J. DuBoff

(57) ABSTRACT

The present invention concerns novel 7-deoxy taxane derivatives their use as antitumor agents, and pharmaceutical formulations.

18 Claims, No Drawings

TAXANE ANTICANCER AGENTS

This application claims benefit of U.S. Ser. No. 60/190,174 Mar. 17, 2000.

BACKGROUND OF THE INVENTION

1. Field of the Invention

The present invention concerns antitumor compounds. More particularly, the invention provides novel paclitaxel derivatives, pharmaceutical formulations thereof, and their use as antitumor agents.

2. Background Art

Paclitaxel is a natural product extracted from the bark of Pacific yew trees, Taxus brevifolia and the active constituent of the anticancer agent TAXOL®. It has been shown to have excellent antitumor activity in in vivo animal models, and recent studies have elucidated its unique mode of action, which involves abnormal polymerization of tubulin and disruption of mitosis. It is used clinically against a number of human cancers. It is an important cancer agent both therapeutically and commercially. Numerous clinical trials are in progress to expand the increase the utility of this agent for the treatment of human proliferative diseases. The results of TAXOL® clinical studies have been reviewed by numerous authors. A very recent compilation of articles by a number of different authors is contained in the entire issue of Seminars in Oncology 1999, 26 (1, Suppl 2). Other examples are such as by Rowinsky et al. in TAXOL®: A Novel Investigational Antimicrotubule Agent, J. Natl. Cancer Inst., 82: pp 1247–1259, 1990; by Rowinsky and Donehower in "The Clinical Pharmacology and Use of Antimicrotubule Agents in Cancer Chemotherapeutics," Pharmac. Ther., 52:35–84,1991; by Spencer and Faulds in "Paclitaxel, A Review of its Pharmacodynamic and Pharmacokinetic Properties and Therapeutic Potential in the Treatment of Cancer," Drugs, 48 (5) 794–847,1994; by K. C. Nicolaou et al. in "Chemistry and Biology of TAXOL®," Angew. Chem., Int. Ed. Engl., 33: 15–44, 1994: by F. A. Holmes, A. P. Kudelka, J. J. Kavanaugh, M. H. Huber. J. A. Ajani, V. Valero in the book "Taxane Anticancer Agents Basic Science and Current Status" edited by Gunda 1. Georg, Thomas T. Chen, lwao Ojima, and Dolotrai M. Vyas, 1995, American Chemical Society, Washington, D.C., 31–57; by Susan G. Arbuck and Barbara Blaylock in the book "TAXOL® Science and Applications" edited by Mathew Suffness, 1995, CRC Press Inc., Boca Raton, Fla., 379–416; and also in the references cited therein.

A semi-synthetic analog of paclitaxel named docetaxel has also been found to have good antitumor activity and is the active ingredient of the commercially available cancer agent TAXOTERE®. See, Biologically Active Taxol Analogues with Deleted A-Ring Side Chain Substitutents and Variable C-2' Configurations, J. Med. Chem., 34, pp 1176–1184 (1991); Relationships between the Structure of Taxol Analogues and Their Antimitotic Activity, J. Med. Chem., 34. pp 992–998 (1991). A review of the clinical activity of TAXOTERE® by Jorge E. Cortes and Richard Pazdur has appeared in Journal of Clinical Oncology 1995, 13(10), 2643 to 2655. The structures of paclitaxel and docetaxel are shown below along with the conventional numbering system for molecules belonging to the class; such numbering system is also employed in this application.

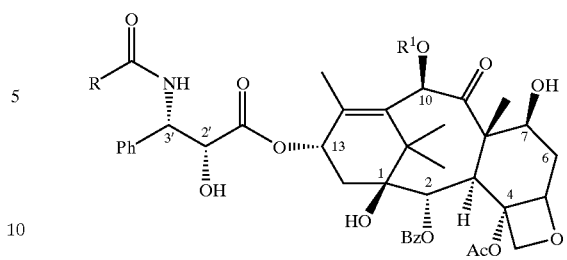

paclitaxel (TAXOL®): R=Ph; R'=acetyl
docetaxel (TAXOTERE®): R=t-butoxy; R'=hydrogen The intention of this invention is to provide new 7-deoxy taxane analogs with useful anticancer properties. Some of the background art pertaining to this invention are shown below.

Several Publications have described the synthesis or attempted synthesis of the 7-deoxy analog of paclitaxel. These are:

Chen, Shu Hui; Huang, Stella; Kant, Joydeep; Fairchild, Craig Wei, Jianmei; Farina, Vittorio. "Synthesis of 7-deoxy- and 7,10-dideoxytaxol via radical intermediates". J. Org. Chem., 58(19). 5028–9, 1993.

Chaudhary, Ashok G.; Rimoldi, John M.; Kingston, David G. I. "Modified taxols. 10. Preparation of 7-deoxytaxol, a highly bioactive taxol derivative, and interconversion of taxol and 7-epi-taxol". J. Org. Chem., 58(15), 3798–9, 1993.

Matovic, Radomir; Saicic, Radomir N. "An efficient semisynthesis of 7-deoxypaclitaxel from taxine". Chem. Commun. (Cambridge). (16), 1745–1746, 1998.

A U.S. patent (U.S. Pat. No. 5,478,854) covering certain deoxy taxanes issued on Dec 26th 1995 by Farina et. al.

A published PCT international application (WO 94/17050) from Holton et. al. discloses 7-deoxy taxane derivatives. Other than actual supporting examples already claimed in the above mentioned U.S. patent, this application discloses many multitudes of hypothetical 7-deoxy taxane analogs with no indication of which compounds would really be useful. This application also does not provide details of the preparation of any C-7 deoxy taxanes which are not covered by the above mentioned U.S. patent. Corresponding U.S. Pat. No. 5,271,268 to Holton et al was granted.

An issued U.S. patent (U.S. Pat. No. 5773461) by Wittman et. al. claims 7-deoxy taxane analogs with unique functional groups at the 6 position as antitumor agents.

A published PCT application (WO 9828288) by Staab et. al. published Jul. 2, 1998, corresponding to U.S. Pat. No. 5,977,386 granted Nov. 2, 1999, describes C-7 deoxy taxanes with thio substituents at the 6 position.

A published PCT application (WO 9838862) by Wittman et. al. published Sep. 11, 1998, corresponding to U.S. Pat. No. 5,912,264 granted Jun. 15, 1998, describes C-7 deoxy taxanes with halogen or nitro substituents on C-6.

Nondeoxy analogs with a 3' furyl amide substituent on the sidechain have appeared in both the patent (U.S. Pat. No. 5227,400 and U.S. Pat. No. 5,283,253) and chemistry literature Georg, Gunda I.; Harriman, Geraldine C. B.; Hepperle, Michael; Clowers, Jamie S.; Vander Velde, David G.; Himes, Richard H. Synthesis, Conformational Analysis, and Biological Evaluation of Heteroaromatic Taxanes. J. Org. Chem. (1996), 61(8), 2664–76. Importantly, we are unaware of any reports describing the synthesis of a 7-deoxy analog with this 3'N furoylamide sidechain or any of their novel, useful anticancer properties such as those described by this invention.

Hydroxylation of the 3' sidechain phenyl group of paclitaxel has been reported to lead to reduced potency and thus has been inferred to result in less activity as discussed in the following examples: Wright, M.; Monsarrat, B.; Royer, I.; Rowinsky, E. K.; Donehower, R. C.; Cresteil, T.; Guenard, D. Metabolism and pharmacology of taxoids. Pharmacochem. Libr. (1995), Volume Date 1995, 22 131–64; Sparreboom, Alexander; Huizing, Manon T.; Boesen, Jan J. B.; Nooijen, Willem J.; van Tellingen, Olaf; Beijnen, Jos H. Isolation, purification, and biological activity of mono- and dihydroxylated paclitaxel metabolites from human feces. Cancer Chemother. Pharmacol. (1995). 36(4), 299–304.

Monsarrat, Bernard; Mariel, Eric; Cros, Suzie; Gares, Michele, Guenard, Daniel; Gueritte-Voegelein, Francoise; Wright, Michel. Taxol metabolism. Isolation and identification of three major metabolites of taxol in rat bile. Drug Metab. Dispos. (1990), 18(6), 895–901.

The synthetic preparation of the parahydroxylated 3'phenyl metabolite has been described in the literature. Park, Haeil; Hepperle, Michael; Boge, Thomas C.; Himes, Richard H.; Georg, Gunda I. Preparation of Phenolic Paclitaxel Metabolites. J. Med. Chem. (1996), 39(14), 2705–2709. We are not aware of any published reports of synthetic analogs with phydroxy phenyl 3' sidechains that are purported to have activity advantages.

However, one reference in the patent literature mentions in passing that the para hydroxy phenyl metabolite might have an improved therapeutic index despite reduced potency and thus it's formation in vivo may be fortuitous. Broder et.al. PCT Int. Appl. WO 9715269 published May 1, 1997.

However, this patent does not describe the synthesis or administration of para-hydroxyphenyl taxanes nor any actual efficacy results. Thus, the art clearly shows that the phydroxy phenyl sidechain analog of paclitaxel will be less potent than the parent drug. Most significantly, we are unaware of any prior art which describes the synthesis of novel 7-deoxy taxanes with a 3'parahydroxyphenyl containing sidechain or which describes their novel and unexpected antitumor properties such as those contained in this application.

Both TAXOL® and TAXOTERE® have no oral activity in human or animal models as mentioned in the following prior art on taxanes and modulators. Methods for administering taxanes in the presence of modulators have been been reported to increase the amount of taxanes in the plasma after oral administration: Terwogt, Jetske M. Meerum; Beijnen, Jos H.; Ten Bokkel Huinink, Wim W.; Rosing, Hilde; Schellens, Jan H. M. Co-administration of cyclosporin enables oral therapy with paclitaxel. Lancet (1998), 352(9124), 285.

Hansel, Steven B. A method of making taxanes orally bioavailable by coadministration with cinchonine. PCT Int. Appl. WO 9727855 published Aug. 7, 1997.

Broder, Samuel; Duchin, Kenneth L.; Selim, Sami. Method and compositions for administering taxanes orally to human patients using a cyclosporin to enhance bioavailability. PCT Int. Appl. WO 9853811 published Dec. 3, 1998. These reports contain no antitumor efficacy data but the presence of taxanes in the plasma is extrapolated to show their potential for anaticancer utility.

At least one report of oral activity of taxane analogs or prodrugs in preclinical animal models has appeared in the prior art: Scola, Paul M.; Kadow, John F.; Vyas, Dolatrai M. Preparation of paclitaxel prodrug derivatives. Eur. Pat. Appl. EP 747385 published Dec. 11, 1996. The oral bioavailability of the prodrug which had oral efficacy was not disclosed and no further reports of these compounds progressing to man have appeared. Thus it is clear that taxanes with both good oral bioavailability and good oral efficacy are at minimum, exceedingly rare. There are no such compounds which have been reported to demonstrate both oral bioavailbility and anticancer activity in man.

Several Publications have described the synthesis or attempted synthesis of some 7-deoxy taxane analogs and these are included only because they are additional references in the area of 7-deoxy taxanes.

Chen, Shu Hui; Huang, Stella; Kant, Joydeep; Fairchild, Craig; Wei, Jianmei; Farina, Vittorio. "Synthesis of 7-deoxy- and 7,10-dideoxytaxol via radical intermediates". J. Org. Chem., 58(19), 5028–9, 1993.

Chaudhary, Ashok G.; Rimoldi, John M.; Kingston, David G. I. "Modified taxols. 10. Preparation of 7-deoxytaxol, a highly bioactive taxol derivative, and interconversion of taxol and 7-epi-taxol". J. Org. Chem., 58(15). 3798–9, 1993.

Matovic, Radomir; Saicic, Radomir N. "An efficient semisynthesis of 7-deoxypaclitaxel from taxine". Chem. Commun. (Cambridge), (16), 1745–1746, 1998.

Chen, Shu Hui; Wei, Jian Mei; Vyas, Dolatrai M.; Doyle, Terrence W.; Farina, Vittorio. "A facile synthesis of 7,10-dideoxytaxol and 7-epi-10-deoxytaxol". Tetrahedron Lett., 34(43), 6845–8, 1993.

Poujol, Helene; Al Mourabit, Ali; Ahond, Alain; Poupat, Christiane; Potier, Pierre. "Taxoids: 7-dehydroxy-10-acetyldocetaxel and novel analogs prepared from yew alkaloids". Tetrahedron, 53(37), 12575–12594, 1997.

Poujol, Helene; Ahond, Alain; Mourabit, Ali Al; Chiaroni, Angele; Poupat, Christiane; Potier, Claude Riche Et Pierre "Taxoids: novel 7-dehydroxydocetaxel analogs prepared from yew alkaloids". Tetrahedron, 53(14), 5169–5184, 1997.

Wiegerinck, Peter H. G.; Fluks, Lizette; Hammink, Jeannet B.; Mulders, Suzanne J. E.; de Groot, Franciscus M. H.; van Rozendaal, Hendrik L. M.; Scheeren, Hans W. "Semisynthesis of Some 7-Deoxypaclitaxel Analogs from Taxine B". J. Org. Chem., 61(20), 7092–7100, 1996.

Magnus, Philip; Booth, John; Diorazio, Louis; Donohoe, Timothy; Lynch, Vince; Magnus, Nicholas; Mendoza, Jose; Pye, Philip; Tarrant, James. "Taxane diterpenes. 2: Synthesis of the 7-deoxy ABC taxane skeleton, and reactions of the A-ring". Tetrahedron, 52(45), 14103–14146, 1996.

Magnus, Philip; Booth, John; Diorazio, Louis; Donohoe, Timothy; Lynch, Vince; Magnus, Nicholas; Mendoza, Jose; Pye, Philip; Tarrant, James. "Taxane diterpenes. 2: Synthesis of the 7-deoxy ABC taxane skeleton and reactions of the A-ring". Tetrahedron, 52(45), 14103–14146, 1996.

Tarrant, James Giles. "Studies directed towards the total synthesis of 7-deoxytaxol: synthesis of the tricyclic core of taxol". (1995), 303 pp. CAN 125:168367; AN 1996:406672 CAPLUS.

SUMMARY OF INVENTION

This invention relates to novel antitumor compounds represented by formula I, or pharmaceutical salts thereof

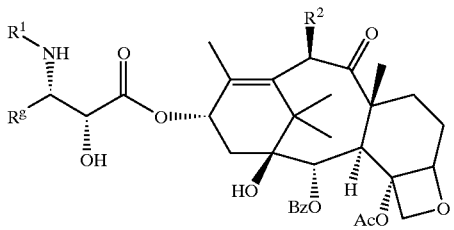

wherein $R^1$ is —$COR^z$ in which $R^z$ is RO—, R, or heteroaryl, with the proviso that $R^z$ must be heteroaryl unless either (1) $R^g$ is $R^k$ or $R^2$ is —$OCOR^b$, or (2) $R^g$ is $R^k$ and $R^2$ is —OC(O)$R^b$;

$R^g$ is $C_{3-6}$ alkyl, $C_{3-6}$ alkenyl, $C_{3-6}$ alkynyl $C_{3-6}$ cycloalkyl, $R^k$, or a radical of the formula —W—$R^x$ in which W is a bond, or —(CH$_2$)$_t$—, in which t is one or 2;

$R^x$ is phenyl or heteroaryl, and furthermore $R^x$ can be optionally substituted with one to three same or different $C_{1-6}$alkyl, $C_{1-6}$alkoxy, halogen or —CF$_3$ groups;

$R^k$ is a radical of the formula —W—$R^s$ in which W is a bond, or —(CH$_2$)$_t$—, in which t is one or 2; and $R^s$ is phenyl substituted with hydroxy;

$R^2$ is —OCOR, H, OH, —OR, —OSO$_2$R, —OCONR$^o$R, —OCONHR, —OCOO(CH$_2$)$_t$R, —OCOOR, or—OCOR$^b$;

R and $R^o$ are independently $C_{1-6}$ alkyl, $C_{3-6}$ cycloalkyl, benzyl, or phenyl, optionally substituted with either one hydroxy group or with one to three same or different $C_{1-6}$ alkyl, $C_{1-6}$ alkoxy, halogen or —CF$_3$ groups; and $R^b$ is -morpholino, -nheptyl, —CH$_2$OPh,—(2-nitrophenyl), —CH=CHPhenyl or —(2-aminophenyl).

Another aspect of the present invention provides a method for inhibiting tumor in a mammalian host which comprises administering to said mammalian host an antitumor effective amount of a compound of formula I. The method of administration may be oral or intravenous or any other suitable route.

Yet, another aspect of the present invention provides a pharmaceutical formulation which comprises an antitumor effective amount of a compound of formula I in combination with one or more pharmaceutically acceptable carriers, excipients, diluents or adjuvants.

Yet, another aspect of the present invention provides a process for preparing 7-deoxy taxanes or baccatins by hydrogneation of the corresponding 6,7-olefin taxane intermediates.

DETAILED DESCRIPTION OF THE INVENTION

In the application, unless otherwise specified explicitly or in context, the following definitions apply. In this application, the symbols once defined retain the same meaning throughout the application, until they are redefined.

The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms. examples include ethynyl, propynyl, butynyl, and hexynyl. As used herein t-butyloxy and t-butoxy are used interchangeably.

"Aryl" means aromatic hydrocarbon having from six to ten carbon atoms; examples include phenyl and naphthyl. "Substituted aryl" means aryl independently substituted with one to five (but preferably one to three) groups selected from $C_{1-6}$ alkanoyloxy, hydroxy, halogen, $C_{1-6}$ alkyl, trifluoromethyl, $C_{1-6}$ alkoxy, aryl, $C_{2-6}$ alkenyl, $C_{1-6}$ alkanoyl, nitro, amino, cyano, azido, $C_{1-6}$ alkylamino, di-$C_{1-6}$ alkylamino, and amido. "Halogen" means fluorine, chlorine, bromine, and iodine.

"Heteroaryl" means a five- or six-membered aromatic ring containing at least one and up to four non-carbon atoms selected from oxygen, sulfur and nitrogen. Examples of heteroaryl include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, and like rings "Hydroxy protecting groups" include, but are not limited to, ethers such as methyl, t-butyl, benzyl, p-methoxybenzyl, p-nitrobenzyl, allyl, trityl, methoxymethyl, methoxyethoxymethyl, ethoxyethyl, 1-methyl-1-methoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyldimethylsilyl ether, dialkyl alkoxy silyl ethers such as diisopropyl methoxy silyl ethers; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, benzyl, and p-nitrophenyl. Additional examples of hydroxy protecting groups may be found in standard reference works such as Greene and Wuts, Protective Groups in Organic Synthesis, 3rd Ed., 1999, John Wiley & Sons, and McOmie; and Protective Groups in Organic Chemistry, 1975, Plenum Press.

"Ph" means phenyl; "ipr" means isopropyl;

The substituents of the substituted alkyl, alkenyl, alkynyl, aryl, and heteroaryl groups and moieties described herein, may be alkyl, alkenyl, alkynyl, aryl, heteroaryl and/or may contain nitrogen, oxygen, sulfur, halogens and include, for example, lower alkoxy such as methoxy, ethoxy, butoxy, halogen such as chloro or fluoro, nitro, amino, and keto.

A preferred embodiment are compounds I, or pharmaceutically acceptable salts thereof in which $R^2$ is —OC(O)$R^b$; and $R^g$ is phenyl, 2-furyl, 2-thienyl $C_{3-6}$ alkyl, $C_{3-6}$ alkenyl, $C_{3-6}$ cycloalkyl,or $R^s$; where t=0 and $R^s$ is parahydroxyphenyl; and $R^z$ is tBuO—, phenyl, or 2-Furyl.

Another preferred embodiment are compounds I, or pharmaceutically acceptable salts thereof in which $R^2$ is —OCOR, H, OH, —OR, or —OCOOR; and $R^g$ is $R^s$; and $R^z$ is $C_{1-6}$alkyloxy, phenyl, or heteroaryl.

An even more preferred embodiment are compounds I, or pharmaceutically acceptable salts thereof in which $R^2$ is hydrogen, hydroxy, or acetyloxy; $R^g$ is parahydroxyphenyl; and $R^1$ is $C_{3-6}$alkyloxycarbonyl.

Another preferred embodiment are compounds I, or pharmaceutically acceptable salts thereof in which $R^z$ is 2-furyl, 3-furyl, 2-thienyl, or 3-thienyl; $R^2$ is hydrogen, hydroxy or acetyloxy; and $R^g$ is phenyl, 2-furyl, 2-thienyl $C_{3-6}$ alkyl, $C_{3-6}$ alkenyl, $C_{3-6}$ cycloalkyl, or $R^k$ where t=0 and $R^s$ is parahydroxyphenyl;

A most preferred embodiment are compounds I, or pharmaceutically acceptable salts thereof in which $R^z$ is 2-furyl or 3-furyl; and $R^2$ is acetyloxy; and $R^g$ is phenyl, $C_{3-6}$ alkyl, or $C_{3-6}$ cycloalkyl;

The new products that have the general formula I display a significant inhibitory effect with regard to abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis: solid tumors; ovarian, breast, brain, prostate, colon, stomach, kidney, and/or testicular cancer, Karposi's sarcoma; cholangiocarcinoma; choriocarcinoma: neuroblastoma; Wilm's tumor, Hodgkin's disease; melanomas; multiple myelomas; chronic lymphocytic leukemias; and acute or chronic granulocytic lymphomas. The novel products in accordance with the invention are particularly useful in the treatment of non-Hodgkin's lymphoma, multiple myeloma, melanoma, and ovarian, urothelial, oesophageal, lung, and breast cancers. The products in accordance with the invention can be utilized to prevent or delay the appearance or reappearance, or to treat these pathological conditions. In addition, the compounds of formula I are useful in treating and/or preventing polycystic kidney diseases (PKD) and rheumatoid arthritis. The compounds of this invention may also be useful for the treatment of Alzheimer's disease. While some of the products of general formula I are of interest due to advantages over commercial taxanes following iv administration others are of interest due to their unique properties after oral administration.

The compounds of this invention can be made by techniques from the conventional organic chemistry repertoire. Schemes I–V, which depict processes that compounds within the scope of formula I can be made, are only shown for the purpose of illustration and are not to be construed as limiting the processes to make the compounds by any other methods.

DETAILED DESCRIPTION OF INVENTION

A compound of formula I may be produced by the processes as depicted in Schemes I–IV which follow. The methods can be readily adapted to variations in order to produce compounds within the scope of formula but not specifically disclosed. Further variations of the methods to produce the same compounds in somewhat different fashion will also be evident to one skilled in the art.

One of the ways the compounds of this invention can be made is by the general method which shown is Scheme I. In Step (a) of the scheme, azetidinone IV is reacted with a compound of formula II (a baccatin III derivative®). The general class of azetidinones (β-lactams) of formula IV are well known. Methods for preparing suitably substituted β-lactams can be found in U.S. Pat. No. 5,175,315, European patent application 0 590 267 A2, the other U.S. patents or literature mentioned above, or references therein by Ojima et al. in Tetrahedron, 48, No. 34, pp 6985–7012 (1992); Journal of Organic Chemistry, 56, pp 1681–1683 (1991); and Tetrahedron Letters, 33. No. 39, pp 5737–5740 (1992); by Brieva et al. in J. Org. Chem., 58, pp 1068–1075; by Palomo et al. in Tetrahedron Letters, 31, No. 44, pp 6429–6432 (1990); and in Rey, Allan W.; Droghini, Robert; Douglas, James L.; Vemishetti, Purushotham; Boettger, Susan D.; Racha, Saibaba; Dillon, John L. Can. J. Chem. 72(10), 2131–6 (1994).

All disclosures are herein incorporated by reference in their entirety. The methods that can be adapted to variations in order to produce other azetidinones within the scope of formula IV, but not specifically disclosed herein or in the above references or reported elsewhere, will be obvious to anyone skilled in the art.

The baccatin III derivatives (II) can be attached to a sidechain using any of the methodology which is now already well known in the art. The many references cited in this invention disclosure and Tetrahedron, 48, No. 34, pp 6985–7012 (1992) describe processes whereby the class of azetidinones of formula IV are reacted with (C)13-hydroxy group of baccatin III derivatives or metal alkoxide thereof to afford taxane analogues with a variety of (C)13-side chains. In Step (a) of Scheme I, it is advantageous to convert the hydroxy group on the (C)13-carbon into a metal alkoxide before the coupling. The formation of a desired metal alkoxide may be done by reacting a compound of formula II with a strong metal base, such as lithium diisopropylamide, $C_{1-6}$ alkyllithium, lithium bis(trimethylsilyl)amide, phenyllithium, sodium hydride, potassium hydrides lithium hydride, or the like base. For example when lithium alkoxide is desired, a compound of formula II may be reacted with n-butyllithium in an inert solvent such as tetrahydrofuran. For examples of attachment of substituted baccatins with a suitably substituted lactam via the method of Holton see U.S. Pat. No. 5,175,315; U.S. Pat. No. 5,466,834; U.S Pat. No. 5,229,526; U.S. Pat. No. 5,274,124; U.S. Pat. No. 5,243,045; U.S. Pat. No. 5,227,400; U.S. Pat. No. 5,336,785, and U.S. Pat. No. 5,254,580, U.S. Pat. No. 5,294,637, or EP 0 590 267 A2. Some examples of using β-lactams to prepare other substituted taxane derivatives are n PCT WO94/14787. This patent also describes an alternative method for attaching substituted isoserine sidechains to substituted baccatins which would be applicable for the compounds of this invention. This same alternate method is described in another publication by Kingston et. al. Tetrahedron Lett. (1994), 35(26), 4483–4. Further information on alternative methods to attach sidechains to baccatins are contained in Thottathil, et.al Eur. Pat. Appl. EP 735036 published Oct. 2, 1996.

Scheme 1

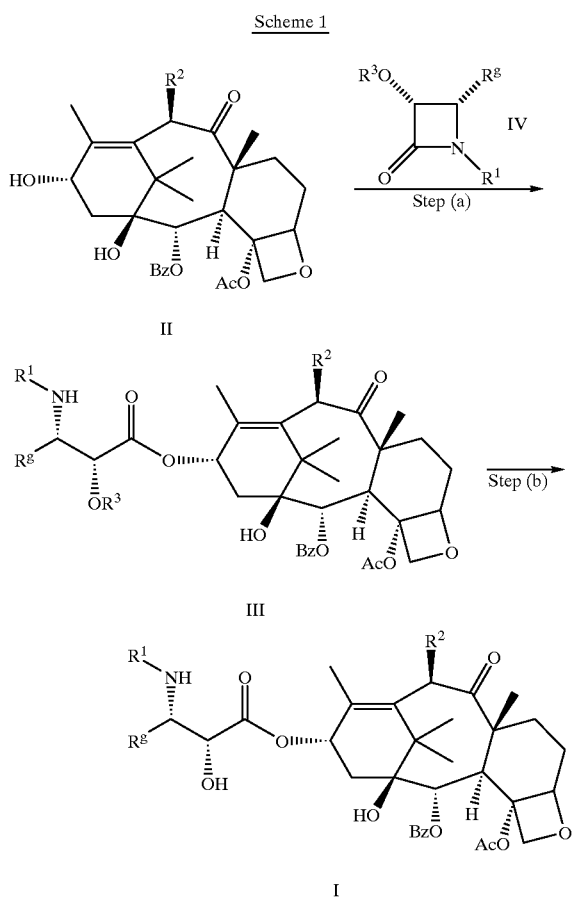

The numbering on baccatin III derivative of formula II as used in this application is as follows:

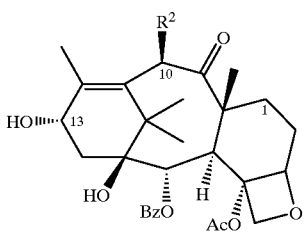

As used herein, $R^3$ is a conventional hydroxy protecting group. Conventional hydroxy protecting groups are moieties which can be employed to block or protect a hydroxy function, and they are well known to those skilled in the art. Preferably, said groups are those which can be removed by methods which result in no appreciable destruction to the remaining portion of the molecule. Examples of such readily removable hydroxy protecting groups include chloroacetyl, methoxymethyl, 1-methyl-1-methoxyethyl, tetrahydropyranyl, tetrahydrothiopyranyl, dialkylsilylethers, such as dimethylsilyl ether, and trialkylsilyl ethers such as trimethylsilyl ether, triethylsilyl ether, and t-butyidimethylsily ether, dialkyl alkoxy silyl ethers such as diisopropyl methoxy silyl ethers; 2,2,2-trichloroethyoxymethyl, 2,2,2-trichloroethyloxycarbonyl (or simply trichloroethyloxycarbonyl), benyloxycarbonyl and the like. Other suitable protecting groups which may be used are found in Chapter 2 of "Protecting Groups in Organic Synthesis", 3rd Ed., by Theodora W. Greene and Peter G. M. Wuts (1999, John Wiley & Sons). A protecting group for formula IV compounds which has been used frequently in the literature is trialkylsilyl. In Step (b), the protecting group R3 is removed. If R3 equals triC1-6alkylsilyl, such as triethylsilyl, it can be removed with fluoride ion or with mineral acid in alcohol or acetonitrile. The removal with fluoride ion is conducted in an inert solvent such as tetrahydrofuran, methylene chloride, 1,4-dioxane, DMF, chloroform, or in the like solvent; and the reaction medium may be buffered with a weak acid such as acetic acid. An example of mineral acid is hydrochloric acid.

In compounds of this invention $R^2$ may also be hydroxy. in compounds where $R^2$ is hydroxy, a suitable protecting group must be utilized prior to sidechain cleavage or installed selectively on the C-10 hydroxy group prior to the coupling reaction. Trialkylsilyl, dialkylalkoxysilyl, CBz, or Troc protecting groups are suitable for this protecting group step and can be attached using methodology which is well known in the art. The protecting groups can ideally be removed simultaneously in step (b) or or in a separate deprotection step immediately preceding or following step (b).

The simple 7-deoxy baccatin core 11 can be prepared as described in the previously mentioned U.S. patent, U.S. Pat. No. 5,478,854 by Farina et al. Alternatively, the desired 7-deoxy baccatin core can be obtained using the chemistry shown in Scheme II. One likely example of a starting material for such a scheme would be paclitaxel in which R=benzoyl, Rg=phenyl and $R^2$=acetoxy.

As shown in Scheme II, the starting material is a known taxane analog. The 2' hydroxy group of a taxane analog with an intact sidechain is suitably protected to leave the most reactive hydroxy group at C-7. Compound 1 in Scheme I is protected at the 2' hydroxy group at the sidechain. Step c describes the protection of the 2' hydroxy group and uses as a 2' tertbutyldimethylsilyl ether as an example. This protecting group is by now well known in the taxane art and has been described by several authors including Kingston and George. The example of compound 1 actually described utilizes this silyl protecting group at the 2' position. Although this group is preferred, other protecting groups can be utilized. The preparation of intermediates arising from step c and step d are now well known in the art. The synthesis of the 7-trifluoromethanesulfonate (triflate) intermediate is shown in step d and is by now well known in the art. The preparation of 7-O triflates and their conversion into cyclopropane and olefin has been divulged by Johnson, R. A., et al., Taxol chemistry. 7-O-Triflates as precursors to olefins and cyclopropanes. *Tetrahedron Letters*, 1994. 35(43): p. 7893–7896 & by the same authors in WO 94/29288. The preferred synthesis utilizes DMAP as the base and triflic anhydride as the activating agent. Experimental details for the preparation of the olefin arising from step d are contained in U.S. Pat. No. 5,773,461. Hydrogenation of the olefin is carried out in step f to provide the 7-deoxy taxane intermediate. Many hydrogenation catalysts could be used for this hydrogenation reaction. Palladium based catalysts such as palladium on carbon or palladium hydroxide are suitable as well as Rhodium, Iridium, or platinum based catalysts. Solvents such as lower molecular weight alcohols are suitable for the reaction. Other inert solvents such as ethyl acetate used alone or as a cosolvent may also be utilized. The hydrogenation may be carried out from 1 to 5 atmospheres of hydrogen.

The preferred conditions are using 10% palladium on carbon catalyst, in ethanol under 65 PSI of hydrogen. The reaction may be run until theoretical amounts of hydrogen are consumed or more typically for excess time such as 48 h or longer,

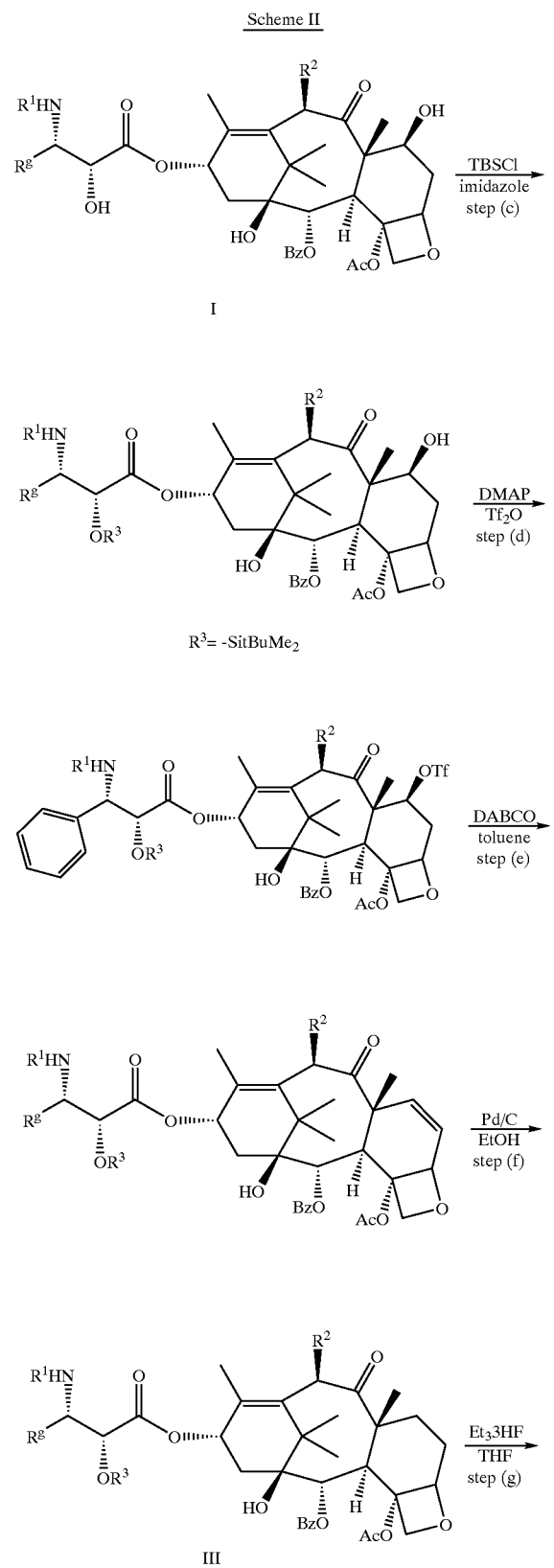

Scheme II

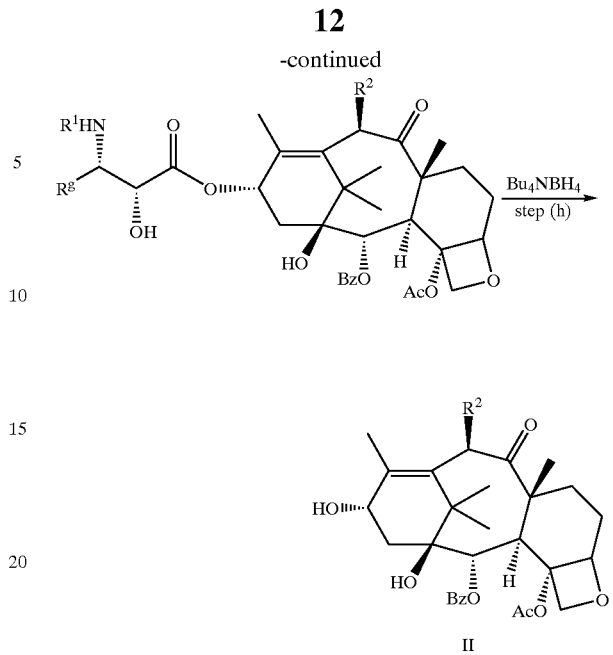

Removal of the 2' TBS protecting group in these compounds as depicted by step g, is effected by triethylamine trihydrofluoride in THF solvent. Other fluoride sources could also be utilized. For example tetrabutyl ammonium fluoride, pyridinium hydrofluoride, potassium fluoride, or cesium fluoride may find utility. The potassium fluoride may be utilized in combination with a complexing agent such as 18-crown-6 or the like to aid in desilylation. A solvent such as acetonitrile is typically used under these conditions. Other conditions such as mild aqueous hydrochloric acid and a cosolvent such as acetonitrile or THF may be useful for deprotection. The same conditions work equally are applicable for other silicon based protecting groups.

Many of the schemes refer to a hydroxy protecting group, preferably a trialkylsilyl group. It is to be understood that hydroxy protecting group may be a carbonate or ester group —C(O)ORx or —C(O)Rx or substituted methyl, ethyl, or benzyl ethers. Thus when such a group is employed as a hydroxy protecting group, it may be removed to generate the free hydroxy protecting group. Many suitable protecting groups can be found in the book "Protective Groups in Organic Synthesis: 3rd ed. by Thedora W. Greene and Peter G. M. Wuts Copyright 1999 by John Wiley and Sons Inc."

Thus deprotection as shown in step g generates compounds I from nondeoxy taxanes. However, removal of the sidechain as shown in step h provides baccatin intermediates II which can be attached to a novel sidechain as shown in Scheme I to generate additional novel compounds I.

As depicted in step h, reaction of I with tetrabutylammonium borohydride via the method of Magri et. al. in J. Org. Chem. 1986, 51, pp. 3239–3242 provides the substituted baccatin derivatives. For examples of the use of the Magri methodology to prepare other 7-substituted baccatins see U.S. Pat. No. 5,254,580 or U.S. Pat. No. 5,294.637.

Another aspect of the invention involves the synthesis of compounds I with novel substituents $R^2$ at the C-10 position. As shown in Scheme III, these compounds can be prepared by selective hydrolysis of a C-10 acetyl group of compounds I to generate compounds IV. Alternatively, compounds IV can be directly prepared as described in Scheme I by utilizing a C-10 protecting group on the baccatin core II and then deprotecting the protecting group after sidechain attachment.

Scheme III

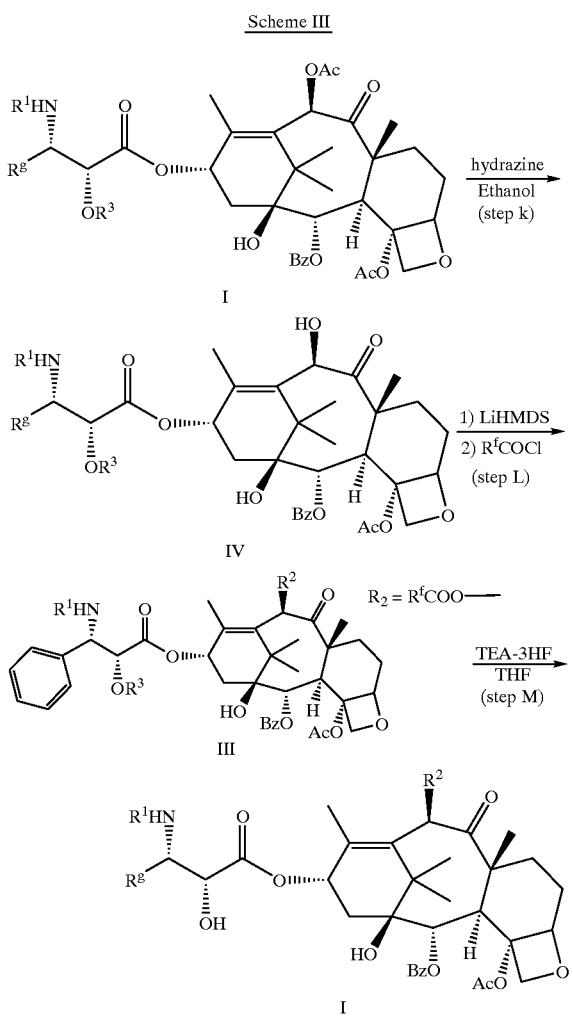

group. A particularly useful base for Step (a) is a strong base such as C1–6alkyllithium, lithium bis(trimethylsily)amide, or the like base used in about 1.1 equivalent amount. The deprotonation by base is preferably conducted in aprotic solvent, such as tetrahydrofuran, at low temperature, usually in the range from −40° to 0° C. The substituents are attached to the C-10 deprotonated hydroxyl group (alkoxide)in step L using R$^f$C(O)Cl or the corresponding acid bromide or anhydride. Compounds III are then converted to I by the methodology described previously.

An alternative preparation of compounds I is depicted in Scheme IV. The preparation of the amine intermediate VI is described in the examples and is carried out by methodology which is well known in the art. The amine intermediate VI is dissolved in an inert solvent such as ethyl acetate and a base such as sodium bicarbonate is added. A stoichiometric or slightly greater amount of most preferably an acid chloride or alternatively acid anhydride is added to provide compound I directly.

Scheme IV

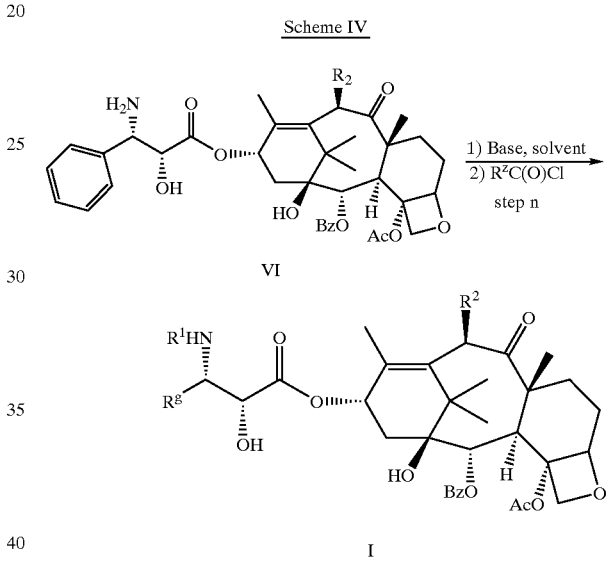

The selective deesterification of taxanes at the C-10 position via hydrazinolysis has been published: Datta, Apurba; Hepperle, Michael; Georg, Gunda I. Selective Deesterification Studies on Taxanes: Simple and Efficient Hydrazinolysis of C-10 and C-13 Ester Functionalities. J. Org. Chem. (1995), 60(3), 761–3. An alternate reference in the literature describes the use of basic hydrogen peroxide with similar results.

Several references for the prepartion of C-10 analogs have appeared in the art and these are, Holton, Robert A.; Chai, Ki Byung. C-10 Taxane derivatives and pharmaceutical compositions containing them as antileukemia and antitumor agents. PCT Int. Appl. 60 pp WO 9415599 Jul. 21, 1994.

Rao, K. V.; Bhakuni, R. S.; Oruganti, R. S. J. Med. Chem. 1995 38, 3411–3414.

Kant, J.; O'Keeffe, W. S.; Chen, S-H.; Farina, V.; Fairchild, C.; Johnston, K.; Kadow, J. F; Long, B. H.; Vyas, D. A. Tetrahedron Letts. 1994, 35, 5543–5546.

Ojima, I.; Slater, J. C.; Michaud, E.; Kuduk, S. D.; Bounaud, P-Y.; Vrignaud, P.; Bissery, M-C.; Veith, J. M. Pera, P. Bernacki. R. J. J. Med. Chem. 1996, 39, 3889–3896.

Using the methodology described in Scheme III or the abovementioned art, C-10 substituents covered by this invention were installed. A base is normally required in Step (L) to initially deprotonate a proton from C-10 hydroxy The specific examples that follow illustrate the syntheses of the compounds of the instant invention, and is not to be construed as limiting the invention in sphere or scope. The method may be adapted to variations in order to produce the compound embraced by this invention but not specifically disclosed. Further, variations of the methods to produce the same compound in somewhat different manner will also be evident to one skilled in the art.

In the following experimental procedures, all temperatures are understood to be in Centigrade (C) when not specified. The nuclear magnetic resonance (NMR) spectral characteristics refer to chemical shifts (d) expressed in parts per million (ppm) versus tetramethylsilane (TMS) as reference standard. The relative area reported for the various shifts in the proton NMR spectral data corresponds to the number of hydrogen atoms of a particular functional type in the molecule. The nature of the shifts as to multiplicity is reported as broad singlet (bs or br s), broad doublet (bd or br d), broad triplet (bt or br t), broad quartet (bq or br q), singlet (s), multiplet (m), doublet (d), quartet (q), triplet (t), doublet of doublet (dd), doublet of triplet (dt), and doublet of quartet (dq). The solvents employed for taking NMR spectra are acetone-d6 (deuterated acetone). DMSO-d6 (perdeuterodimethylsulfoxide), D2O (deuterated water), CDCl3 (deuterochloroform) and other conventional deuterated solvents. The infrared (IR) spectral description include only absorption wave numbers (cm−1) having functional group identification value Celite is a registered trademark of the Johns-Manville Products Corporation for diatomaceous earth.

Silica gel used in the following experimentals is silica gel 60 with a particle size 230–400 mesh obtained from EM Separations Technology.

The abbreviations used herein are conventional abbreviations widely employed in the art. Some of which are: DAB (deacetylbaccatin III); MS (mass spectrometry); HRMS (high resolution mass spectrometry); Ac (acetyl); Ph (phenyl); v/v (volume/volume); FAB (fast atom bombardment); NOBA (m-nitrobenzyl alcohol); min (minute(s)); h or hr(s) (hour(s)); DCC (1,3-dicyclohexylcarbodiimide); BOC (t-butoxycarbonyl); CBZ or Cbz (benzyloxycarbonyl); Bn (benzyl); Bz (benzoyl); Troc (2,2,2-trichloroethyloxycarbonyl), DMS (dimethylsilyl), TBAF (tetrabutylammonium fluoride), DMAP (4-dimethylaminopyridine); TES (triethylsilyl); DMSO (dimethylsulfoxide); THF (tetrahydrofuran); HMDS (hexamethyidisilazane); MeOTf (methyltriflate); NMO (morpholine-N-oxide); (DHQ)2PHAL (hydroquinine 1,4-phthalazinediyl diether). Tf=triflate=trifluoromethanesulfonate; LRMS (low resolution mass spectrometry); ESI (electrospray ionization); TEMPO (2,2,6,6-tetramethyl-1-piperidinyloxy, free radical); DBU (diazobicycloundecene); MOMCl (chloromethyl methyl ether); Ac (acetyl); (Ar, aryl); Bz (benzoyl); Cbz (benzyloxycarbonyl); DCI (desorption chemical ionization); DMF (dimethylformamide); DMSO (dimethyl sulfoxide); FAB (fast atom bombardment); H (hour(s)); HRMS (high resolution mass spectrometry); LiHMDS (lithium hexamethyidisilazane or lithium bis(trimethylsilyl)amide); HMDS (hexamethyldisilazane); i-PrOH (isopropylalcohol): min (minute(s)); MS (mass spectrometry); Ph (phenyl); rt (room temperature); tBu (tertiarybutyl); TES (triethylsilyl), THF (tetrahydrofuran)TLC (thin layer chromatography) Y (yield) TPAP (tetrapropyl ammonium peruthenate); MCPBA (meta chloroperoxy benzoic acid); LDA (lithium diisopropyl amide); DMF (dimethylformamide); TBS (tert-butyldimethylsilyl); 18-crown-6 (1, 4, 7, 10, 13, 16-hexaoxacyclo-octadecane); DEAD (diethylazodicarboxylate).

EXAMPLE 1

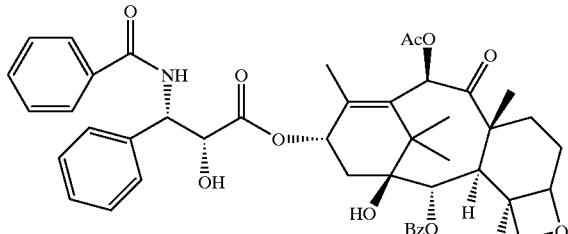

7-Deoxy-paclitaxel. (1) The 2'-O-triethylsilyl-7-deoxy-6,7-olefin of paclitaxel (1.2 g, 1.26 mmol) prepared according to the method of Johnson et al. was dissolved in 20 mL of ethanol and 1.51 g of 10% Pd on carbon added. The solution was shaken under an atmosphere of 65 psi of hydrogen for 48 hours. The catalyst was removed by filtration and the solution concentrated to give 1.192 g of product (quant.). The product (805 mg, 0.845 mmol) in 20 mL of acetonitrile was treated at 0° C. with 1N HCl (1.69 mL, 1.69 mmol) for 1 hour. The solution was diluted with ethyl acetate and washed with saturated bicarbonate and brine. The organic fraction was dried over MgSO4 and concentrated. The residue was chromatographed over silica gel using 1:1 hexane-ethyl acetate to give 655 mg of product (83% overall yield).

ESIMS m/z 838 (M+H) IR(KBr) 3442 (br), 1733, 1715, 1243 cm−1 1H NMR (CDCl3, 300 MHz) δ 8.15 (d, J=7.2 Hz, 2H), 7.72 (d. J=7.2 Hz, 2H), 7.63–7.31 (m, 11H), 6.96 (d, J=9 Hz, 1H), 6.42 (s, 1H), 6.20 (t, J=9 Hz, 1H), 5.79 (d, J=9 Hz, 1H), 5.66 (d, J=7.2 Hz, 1H), 4.92 (d, J=9.6 Hz, 1H), 4.77 (m, 1H), 4.31 (d, J=7.2 Hz, 1H), 3.48 (d, J=5.1 Hz, 1H), 2.44–1.88 (m, 5H), 2.39 (s, 3H), 2.20 (s, 3H), 1.79 (s, 3H), 1.74 (s, 4H), 1.54 (m, 1H), 1.20 (s, 3H), 1.13 (s, 3H). Anal. Calcd for C47H51NO,13: C, 67.37; H, 6.13; N, 1.67. Found: C, 67.56; H, 6.39, N, 1.56.

EXAMPLE 2

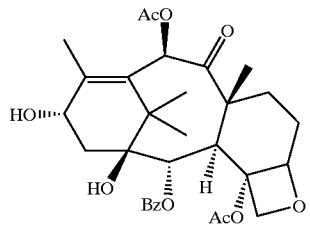

7-Deoxy Baccatin III. (2) To a solution of 7-deoxy paclitaxel (461 mg, 0.55 mmol) in 20 mL of methylene chloride and 0.4 mL of methanol was added Bu4NBH4 (283 mg, 1.1 mmol) and the solution stirred for 24 hours. The solution was quenched with saturated NH4Cl and extracted with ethyl acetate. The solution was dried over MgSO4 and concentrated. The residue was chromatographed over silica gel using hexane-ethyl acetate (1:1) to give 249 mg of product (79%).

FABMS m/z 699 (M+Na) IR(film) 3514 (br), 1734, 1712, 1374, 1274, 1242, 1110, 1070, 1018, 754 cm−1 1H NMR (CDCl3, 300 MHz) δ 8.09 (d, J=8.6 Hz, 2H), 7.58 (t, J=7.3 Hz, 1H), 7.45 (t, J=7.3 Hz, 2H), 6.44 (s, 1H), 5.59 (d, J=7.3 Hz, 1H)m 4.93 (d, J=9.5 Hz, 1H), 4.82 (br t, 1H), 4.22 (ABq, J=37.0, 8.3 Hz, 2H), 3.81 (d, J=7.2 Hz, 1H), 3.27 (d, J=5.7 Hz, 1H), 2.4–1.4 (m, 6H), 2.25 (s, 3H), 2.19 (s, 3H), 1.69 (s, 6H), 1.08 (s, 3H), 1.04 (s, 3H). Anal. Calcd for C,31H,38O, 10: C, 65.25; H, 6.71; N, 0.00. Found: G, 65.06; H, 6.56, N, 0.00.

EXAMPLE 3

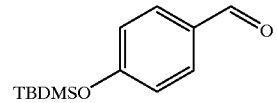

4-(tert-butyidimethylsilanyloxy)benzaldehyde. (3) 4-Hydroxybenzaldehyde (20 g, 0.164 mol) was dissolved in DMF (60 ml) and stirred at RT as imidazole (22.3 g, 0.328 mol) and tert-butyldimethylsilyl chloride (32.1 g, 0.213 mol) were added. The reaction mixture was stirred for 16 h. The solution was diluted with EtOAc, washed with water, brine, then dried (MgSO4) and concentrated in-vacuo to afford 24 g of crude 4-(tert-butyldimethylsilanyloxy)benzaldehyde.

1H NMR (CDCl3) δ 9.87 (1H, s), 7.79–7.76 (2H, m), 6.94–6.92 (2H, m), 0.98 (9H, s), 0.22 (6H, s).

EXAMPLE 4

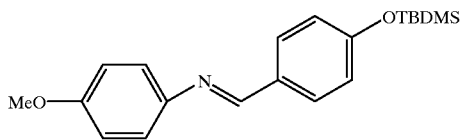

4-methoxy-N-[(4-TBSoxyphenyl)-methylene]-benzenamine. (4) 4-(Tert-Butyldimethylsilanyloxy) benzaldehyde (10 g, 0.081 mol), p-anisidine (24 g, 0.10 mol), and molecular sieves (60 g) were stirred in dichloromethane (160 ml) at RT for 20 h. The solution was filtered, and the filtrate was concentrated in-vacuo to afford 16.5 g of crude 4-methoxy-N-[(4-TBSoxyphenyl)-methylene] benzenamine.

1H NMR (CDCl3) δ 8.42 (1H, s), 7.81–7.78 (2H, m), 7.23–7.21 (2H, m), 6.97–6.92 (4H, m), 3.85 (3H, s), 1.02 (9H, s), 0.25 (6H, s).

EXAMPLE 5

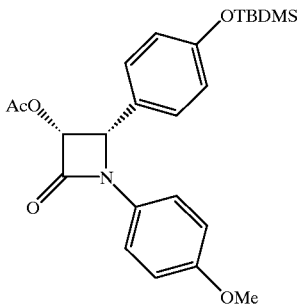

3-(acetyloxy)-4-(4-TBSoxyphenyl)-1-(4-methoxyphenyl)-2-azetidinone. (5) 4-Methoxy-N-[(4-TBSoxyphenyl) methylene]benzenamine (16.5 g, 0.048 mol) was stirred in dichloromethane (300 ml) as triethylamine (16.8 ml, 0.12 mol) was added. The solution was cooled to 0° C., and acetoxyacetyl chloride (6.2 ml, 0.58 mol) was added dropwise over 30 minutes. The reaction mixture was allowed to warm to RT and stirred for 15 hr. The solution was then washed with 0.5N HCl (2×50 ml), water (2×50 ml), brine (50 ml), dried (MgSO4) and concentrated in vacuo. The crude product was purified via flash chromatography (5%–15% EtOAc/Hex) to afford 8.1 g of 3-(acetyloxy)-4-(4-TBSoxyphenyl)-1-(4-methoxyphenyl)-2-azetidinone.

1H NMR (CDCl3) δ 7.31–7.27 (2H, m), 7.18–7.15 (2H, m), 6.83–6.80 (4H, m), 5.89 (1H, d, J=4.8 Hz), 5.29 (1H, d, J=4.8 Hz), 3.76 (3H, s), 1.72 (3H, s), 0.96 (9H, s), 0.18 (6H, s).

EXAMPLE 6

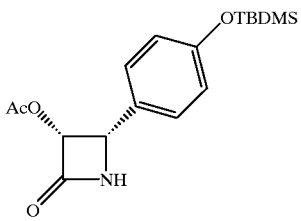

3-(acetyloxy)-4-(4-TBSoxy)phenyl-2-azetidinone (6). Cerric Ammonium Nitrate (29.6 g, 0.054 mol) in water (700 ml) was added dropwise over 30 minutes to a solution of the azetidinone (6.6 g, 0.015 mol) in acetonitrile (500 ml) at 0° C. The reaction was stirred for 20 minutes and then extracted with EtOAc (750 ml, 600 ml). The combined organic layers were washed with sat. NaHCO3 (300 ml, until aqueous phase was neutral), 20% aqueous NaHSO3 (100 ml), 5% aqueous Na2SO3 (100 ml) and brine. Organics dried over MgSO4 and concentrated in-vacuo to provide 3-(acetyloxy)-4-(4-TBSoxy)phenyl-2-azetidinone as a light brown solid.

1H NMR (CDCl3) δ 7.21–7.18 (2H, m), 6.86–6.84 (2H, m), 6.20 (1H, br s), 5.85–5.84 (1H, m), 5.00 (1H, d, J=4.7 Hz), 1.73 (3H, s), 0.99 (9H, s), 0.19 (6H, s).

EXAMPLE 7

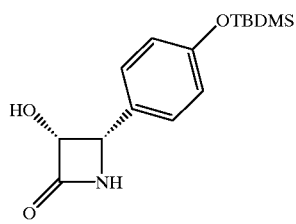

3-hydroxy-4-(4-TBSoxyphenyl)-2-azetidinone. (7) 3-(Acetyloxy)-4-(4-TBSoxy)phenyl-2-azetidinone (840 mg, 2.51 mmol) in methanol (15 ml) was treated with potassium carbonate (115 mg, 0.84 mmol) and stirred for 2 h. The reaction was then neutralized with Dowex resin and filtered. The filtrate was concentrated in-vacuo and purified via flash chromatography to afford 358 mg of 3-hydroxy-4-(4-TBSoxyphenyl)-2-azetidinone.

1H NMR (CDCl3) δ 7.24–7.21 (2H, m), 6.93–6.90 (2H, m), 6.13 (1H, br s), 5.11–5.05 (1H, m), 4.91 (1H, d, J=5.0 Hz), 2.01 (1H, d, J=9.6 Hz), 1.00 (9H, s), 0.21 (6H, s).

EXAMPLE 8

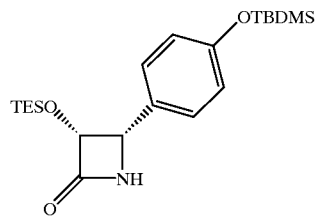

3-TESoxy-4-(4-TBSoxyphenyl)-2-azetidinone. (8) 3-Hydroxy-4-(4-TBSoxyphenyl)-2-azetidinone (358 mg, 1.22 mmol) was dissolved in THF (15 ml), cooled to 0° C. and treated with midazole (155 mg, 2.27 mmol) followed by chloro triethylsilane (0.31 ml, 1.83 mmol). The reaction was stirred for 30 minutes and was then diluted with EtOAc, washed with water and brine, dried (MgSO4) and concentrated in-vacuo to afford 503 mg of 3-TESoxy-4-(4-TBSoxyphenyl)-2-azetidinone.

EXAMPLE 9

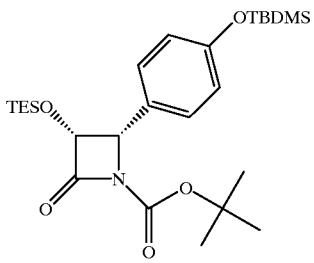

3-TESoxy-4-(4-TBSoxyphenyl)-1-(carboxcylic acid-tert-butyl ester)-2-azetidinone. (9) 3-TESoxy-4-(4-TBSoxyphenyl)-2-azetidinone (480 mg, 1.18 mmol), diisopropylethylamine (0.25 ml, 1.42 mmol), di-tert-butyldicarbonate (309 mg, 1.42 mmol), and 4-DMAP stirred in dichloromethane (10 ml) at 0° C. for 1 h. The solvent was removed in-vacuo at RT and the residue was purified via flash chromatography (8% EtOAc/Hexanes) to afford 586 mg of 3-TESoxy-4-(4-TBSoxyphenyl)-1-(carboxcylic acid-tert-butyl ester)-2-azetidinone.

1H NMR (CDCl3) δ 7.18–7.15 (2H, m), 6.85–6.82 (2H, m), 5.04 (1H, d, J=5.6 Hz), 5.98 (1H, d, J=5.6 Hz), 1.39 (9H, s), 0.99 (9H, s), 0.83–0.78 (9H, m), 0.51–0.43 (6H, m), 0.20 (6H, s).

EXAMPLE 10

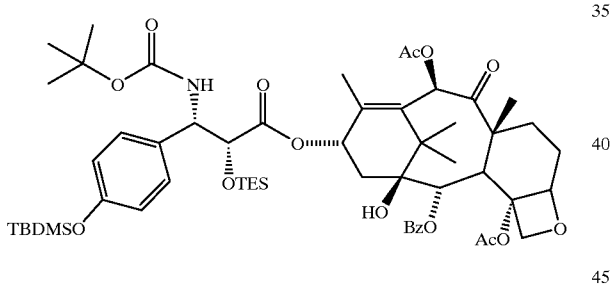

7-deoxy-2'-TES-3'-(4-TBSoxy)phenyl-3'N-t-butoxycarbonyl paclitaxel. (10) 7-Deoxy Baccatin III was stirred in THF (10 ml) at 0° C. and was treated with LiHMDS (0.42 ml, 0.42 mmol, 1M in Hex) followed by the azetidinone from above prepared in Example 9 (355 mg, 0.70 mmol). The reaction was stirred at 0° C. for 1.5 h and was then diluted with EtOAc, washed with water and brine, dried (MgSO4), and concentrated in-vacuo. The residue was purified via flash chromatography (5%–20% gradient elution EtOAc/Hexanes) over SiO2 to afford 138 mg of 7-deoxy-2'-TES-3'-(4-TBSoxy)phenyl-3'N-t-butoxycarbonyl paclitaxel.

¹H NMR (CDCl3) δ 8.17–8.15 (2H, m), 7.64 7.60 (1H, m), 7.54–7.49 (2H, m), 7.15–7.12 (2H, m), 6.87–6.84 (2H, m), 6.50 (1H, s), 6.30–6.27 (1H, m), 5.70 (1H, d, J=7.3 Hz), 5.00–4.97 (1H, m), 4.50 (1H, d, J=1.9 Hz), 4.35 (1H, d, J=8.6 Hz), 4.25 (1H, d, J=8.4 Hz), 3.81 (1H, d, J=7.3 Hz), 2.53–0.19 (66H, including singlets at 2.53, 2.24, 2.06, 1.92, 1.77, 1.18, 3H each).

EXAMPLE 11

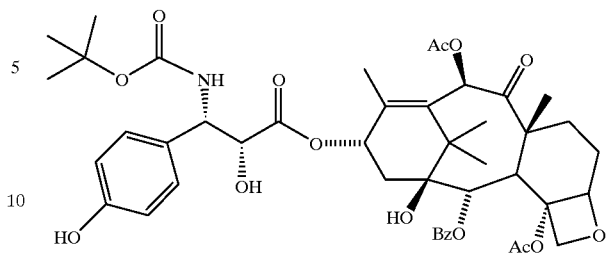

7-deoxy-3'-(4-hydroxyphenyl)-3'N-t-butoxycarbonyl paclitaxel. (Compound Ia)

To 7-Deoxy-2'-TES-3'-(4-TBSoxy)pheryl-3'N-t-butoxycarbonyl paclitaxel (128 mg, 0.12 mmol) in THF (5 ml) was added triethylamine trihydrofluoride (0.08 ml, 0.48 mmol). The solution was stirred at RT for 20 h and was then diluted with EtOAc, washed with sat. NaHCO3, water and brine. The organic layer was dried (MgSO4), concentrated in-vacuo, and purified via flash chromatography (50% EtOAc/Hexanes) to afford 32.2 mg of 7-deoxy-3'-(4-hydroxyphenyl)-3' N-t-butoxycarbonyl paclitaxel. 1H NMR (CDCl3) δ 8.17–8.14 (2H, m), 7.66–7.61 (1H, m), 7.55–7.50 (2H, m), 7.26–7.23 (2H, m), 6.85–6.82 (2H, m), 6.47 (1H, s), 6.26–6.20 (1H, m), 5.69 (1H, d, J=7.3 Hz), 5.34 (1H, d, J=9.2 Hz), 5.22–5.18 (3H, m), 4.97–4.95 (1H, m), 4.59–4.57 (1H, m), 4.34 (1H, d, J=8.3 Hz), 4.24 (1H, d, J=8.3 Hz), 3.78 (1H, d, J=7.2 Hz), 3.34–3.32 (1H, m), 2.40–1.00 (33H, including singlets at 2.40, 2.24, 2.07, 1.86, 1.76, 1.26, 1.00, 3H each).

EXAMPLE 12

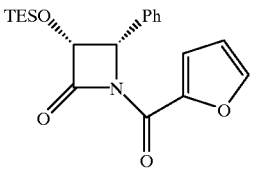

(3R, 4S)-1-(2furoyl)-4-phenyl-3-trimethylsiloxy-2-azetidinone (11) 5 0.44 g (3.60 mmol) 4-DMAP and 5.0 g (18.0 mmol) (3R, 4S)-4-phenyl-3-triethylsilyloxy-2-azetidinone were dissolved in dry dichloromethane (103 ml) and cooled to 0° C. While stirring at 0° C., 6.3 ml (36.0 mmol) diisopropylethylamine was added followed by 1.95 ml (19.8 mmol) furoyl chloride. Solution stirred at 0° C. for 2 h, then was quenched by diluting with dichloromethane and washing with saturated ammonium chloride followed by brine. Organic layer separated, dried over magnesium sulfate, and concentrated in vacuo to afford a yellow oil, Crude product was purified via flash chromatography (5–25% gradient eleution EtOAc/Hex) to afford 3.64 g (54%) desired product. 1H NMR (300 MHz, CDCl3) δ 8.05 (1H, d, J=3.7 Hz), 7.67 (1H, d, J=1.1 Hz), 7.38–7.30 (5H, m), 6.60 (1H, dd, J=1.6, 3.6 Hz), 5.41 (1H, d, J=6.1 Hz), 5.16 (1H, d, J=6.1 Hz), 0.84–0.79 (9H, m), 0.54–0.43 (6H, m),

EXAMPLE 13

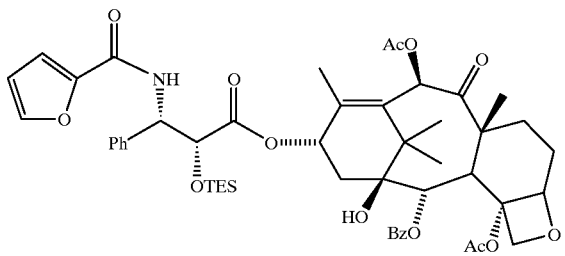

2'-TES-3'N-(2-furoyl)-7-deoxy-paclitaxel. (12) 7-Deoxy Baccatin (800 mg, 1.4 mmol) and 0.78 g (2.1 mmol) of (3R,4S)-1-(2furoyl)-4-phenyl-3-triethylsilyloxy-2-azetidinone (12) were stirred in anhydrous THF (94 ml) at −55° C. as 2.1 ml LiHMDS (1M in Hexanes) was added dropwise. The solution was then warmed to −30° C. over 2 h, and then warmed to −15° C. over 1 h. The reaction was quenched by diluting with EtOAc and washing with saturated ammonium chloride followed by brine. The combined organic extracts were dried over magnesium sulfate and concentrated in vacuo. Purification by flash chromatography (10%–50% EtOAc/Hex gradient elution) afforded 1.2 g (91%) of pure product.

1H NMR (300 MHz, CDCl3) δ 8.19–8.17 (2H, m), 7.63–7.53 (4H, m), 7.49–7.29 (6H, m), 6.95 (1H, d, J=3.6 Hz), 6.46–6.6.44 (2H, m), 6.29–6.23 (1H, m), 5.72–5.67 (2H, m), 4.97–4.94 (1H, m), 4.68 (1H, d, J=2.4 Hz), 4.33 (1H, d, J=8.7 Hz), 4.26 (1H, d, J=8.4 Hz), 3.78 (1H, d, J=7.8 Hz), 2.54–0.73 (33H, including singlets at 2.54, 2.21, 1.85, 1.76, 1.57, 1.23, 1.15, 3H each), 0.56–0.34 (6H, m).

EXAMPLE 14

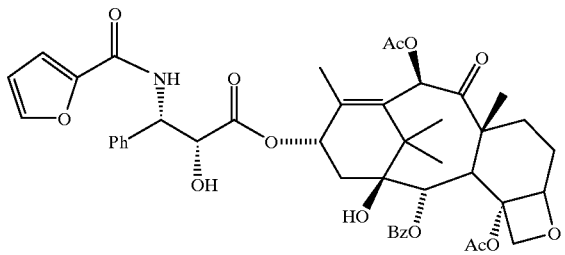

3'N-(2-furoyl)-7-deoxy paclitaxel. (lb) 1.2 g (1.27 mmol) 2'-TES-3'N-furoyl-7-deoxy paclitaxel stirred THF (13 ml) at rt as 0.42 ml (2.54 mmol) triethylamine trihydrofluoride was added. Solution let stir overnight, then was diluted with EtOAc and washed with saturated ammonium chloride followed by brine. Organics dried over MgSO4, concentrated in vacuo, and purified via flash chromatography (20–55% EtOAc/Hex gradient elution) to afford 1.03 g (98%) of desired product.

1H NMR (300 MHz, CDCl3) δ 8.19–8.16 (2H, m), 7.70–7.35 (8H, m), 7.20 (1H, d, J=9.2 Hz), 7.00 (1H, d, J=3.2 Hz), 6.47–6.45 (2H, m), 6.23 (1H, m), 5.75 (1H, dd, J=2.5, 9.1 Hz), 6.68 (1H, d, J=7.3 Hz), 4.92 (1H, dd, J=2.5, 9.4 Hz), 4.78–4.76 (1H, m), 4.31 (1H, d, J=8.4 Hz), 4.24 (1H, d, J=8.5 Hz), 3.77 (1H, d, J=7.3 Hz), 3.66 (1H, d, J=5.3 Hz), 2.44–0.90 (26H, including singlets at 2.44, 2.24, 1.82, 1.76, 1.22, 1.16, 3H each).

EXAMPLE 15

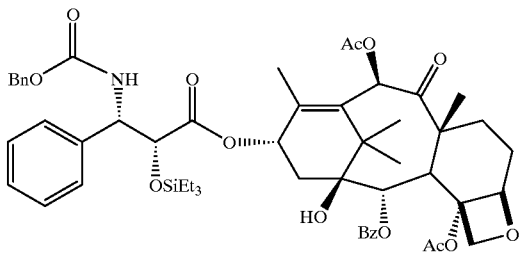

3'N-CBZ-2'-TES-7-deoxy paclitaxel. (13) A hexanes solution of lithium bis (trimethylsilyamide) (4.8 ml, 4.8 mmol) was added to a solution 7-deoxybaccatin (1.6 g) in tetrahydrofuran (28 ml) cooled to −40° C. and the resulting solution was stirred at this temperature for 10 min. A solution of the N-CBZ protected lactam (1.73 g, 4.2 mmol) in tetrahydrofuran (28 ml) was then added and the resulting solution was warmed to 0° C. and stirred for 1.5 h. A TLC evaluation of the reaction mixture at this time indicated the consumption of starting material and the formation of a higher running product. The reaction mixture was then diluted with ethyl acetate and washed with a saturated aqueous ammonium chloride solution followed by brine. The aqueous layers were then back extracted with ethyl acetate and the combined organics were dried over sodium sulfate and concentrated in vacuo. The residual oil was purified via flash chromatography to provide the desired product as a white solid (2.42 g, 88%).

1H NMR (300 MHz, CDCl3) δ 8.18–8.09 (2H, m), 7.63–7.15 (9H, m), 6.46 (1H, s), 6.29–6.26 (1H, m), 5.78 (1H, d, J=9.3 Hz), 5.67 (1H, d, J=7,5 Hz), 5.38–5.25 (1H, m), 5.06–4.91 (3H, m), 4.59 (1H, br s), 4.33 (1H, d, J=8.2 Hz), 4.27 (1H, d, J=8.3 Hz), 3.77 (1H, d, J=7.4 Hz), 2.53–1.16 (29H, including singlets at 2.53, 2.24, 1.88, 1.77, 1.24, 1.16, 3H each), 0.81–0.76 (9H, m), 0.47–0.31 (6H, m).

EXAMPLE 16

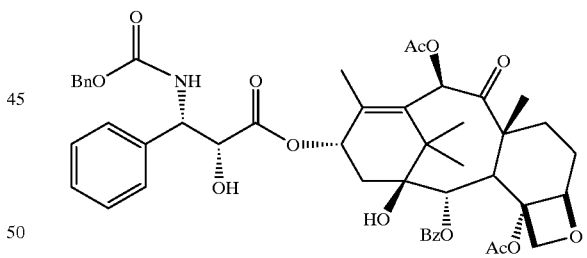

3'N-CBZ-7-deoxy paclitaxel. (14) Triethylamine trihydrofluoride (0.8 ml, 4.9 mmol) was added to a solution of 3'N-CBZ -2'-triethylsilane-7-deoxy paclitaxel (2.4 g, 2.5 mmol) in tetrahydrofuran (30 ml) at room temperature. After 1 h a TLC analysis (hexanes/ethyl acetate, 1/1) indicated the consumption of starting material and the formation of a lower-running product. The reaction mixture was then diluted with ethyl acetate and washed with a solution of saturated aqueous sodium bicarbonate followed by brine. The organics were the dried over sodium sulfate and concentrated in vacuo. The residual oil was purified via flash chromatography to provide the desired compound as a white solid (1.9 g, 89%).

1H NMR (300 MHz, CDCl3) δ 8.18–8.16 (2H, m), 7.65–7.16 (14H, m), 6.45 (1H, s), 6.25–6.21 (1H, m), 5.69–5.66 (2H, m), 5.38 (1H, d, J=9.0 Hz), 5.09–4.93 (3H, m), 4.68 (1H, br s), 4.31 (1H, d, J=8.6 Hz), 4.25 (1H, d, J=8.6 Hz), 3.75 (1H, d, J=7.2 Hz), 3.30 (1H, brs), 2.40–1.16 (24H, including singlets at 2.40, 2.24, 1.84, 1.76, 1.22, 1.16, 3H each).

EXAMPLE 17

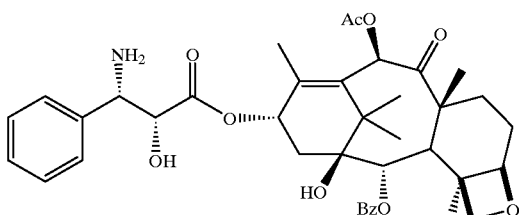

5 3'N-amine-7-deoxy paclitaxel. (15) Ethanol (100 ml) and cyclohlexene (100 ml) were added to 10% Palladium on carbon (2 g) followed by 3'N-CBZ-7-deoxy paclitaxel (1.8 g, 2.1 mmol). The reaction mixture was refluxed for 18 h, then filtered to remove catalyst, and concentrated in vacuo. The crude mixture was purified via flash chromatography to provide the desired compound as a white solid (570 mg, 37%).

1H NMR (300 MHz, CDCl3) δ 8.11–8.08 (2H, m), 7.67–7.64 (1H, m), 7.57–7.52 (2H, m), 7.40–7.24 (6H, m), 6.45 (1H, s), 6.16–6.10 (1H, m), 5.64 (1H, d, J =7.3 Hz), 4.93 (1H, dd, J=2.7, 9.5 Hz), 4.31–4.17 (4H, m), 3.72 (1H, d, J =7.3 Hz), 2.25–1.14 (27H, including singlets at 2.25, 2.23, 1.89, 1.73, 1.22, 1.14, 3H each).

EXAMPLE 18

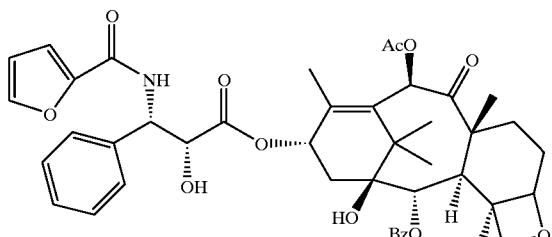

3'N-2furoyl-7-deoxy paclitaxel (Alternate prep of 1b) 3'N-amine-7-deoxy paclitaxel (56 mg, 0.08 mmol) stirred in ethyl acetate (5 ml) at room temperature. To the stirring solution was added saturated sodium bicarbonate (1.25 ml) followed by 2-furoyl chloride (7.5 ml, 0.08 mmol). After stirring vigorously for 10 minutes TLC analysis (ethyl acetate/hexanes, 1/1) indicated the consumption of starting material and the formation of a lower running product. The reaction mixture was diluted with ethyl acetate and washed with a solution of saturated sodium bicarbonate followed by brine. The organics were dried over sodium sulfate and concentrated in vacuo. The crude mixture was purified via flash chromatography to provide the desired compound as a white solid (46 mg, 73%).

EXAMPLE 19

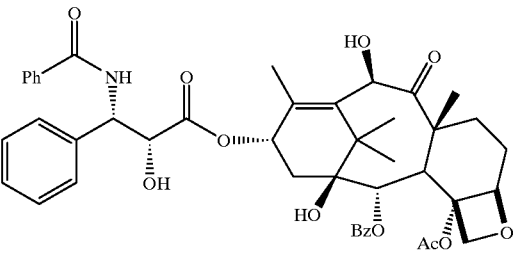

7-Deoxy-10-Desacetyl paclitaxel. (16) To a solution of 2-O-tButyl-dimethyl silyl-7-deoxy paclitaxel (444 mg, 0.467 mmol) in 5 mL of ethanol was added hydrazine (0.30 mL, 9.5 mmol) and stirred from 2.5 hours The solution was diluted with ethyl acetate and washed twice with water and once with brine. The solution was dried over MgSO4 and concentrated. The residue in 10 mL of THF was stirred overnight with triethylamine trihydrofluoride (130 µL). The solution was diluted with ethyl acetate and washed with water and brine, dried over MgSO4 and concentrated. The residue was chromatographed over silica gel using hexane-ethyl acetate (1:1) to give 322 mg of product (85%). Solid material was obtained by adding hexane to a hot solution of the product in ethyl acetate followed by cooling to 0° C.

ESIMS m/z 794(M−H) IR(KBr) 3443, 1745, 1731, 1273, 1273, 1243 cm−1 1H NMR (CDCl3, 300 MHz) δ 8.16 (d, J=7.2 Hz, 2H), 7.75 (d, J=7.2 Hz, 2H), 7.64–7.32 (m, 11H), 7.05 (d, J=9 Hz, 1H), 6.22 (t, J=9.1 Hz, 1H), 5.79 (dd, J=9, 2.7 Hz, 1H), 5.67 (d, J=7.2 Hz, 1H), 5.18 (d, J=1.2 Hz, 1H), 4.93 (d, J=9.9 Hz, 1H), 4.78 (m, 1H), 4.33 (d, J=8.4 Hz, 1H), 4.26 (d, J=8.4 Hz, 1H), 4.19 (s, 1H), 3.82 (d, J=7.5 Hz, 1H), 3.52 (d, J=5.1 Hz, 1H), 2.42 (s, 3H), 2.42 (m, 1H), 2.24 (m, 2H), 2.02 (m, 2H), 1.82 (s, 3H), 1.79 (s, 3H), 1.77 (s, 1H), 1.55 (m, 1H), 1.21 (s, 3H), 1.09 (s, 3H). Anal. Calcd for C,45H,49NO,12: C, 67.91; H, 6.21; N, 1.76. Found: C, 67.88; H, 6.35, N, 1.69.

EXAMPLE 20

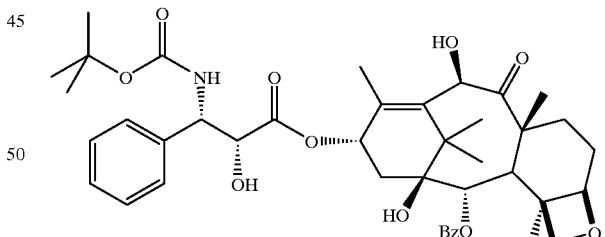

3'N-tButoxycarbonyl-7-deoxy-10-desacetyl-paclitaxel. (17) To a solution of 3'N-tButoxycarbonyl-7-deoxy-paclitaxel (391 mg, 0.469 mmol) in 5 mL of ethanol was added hydrazine (145 µL, 4.62 mmol) and stirred for 1 hour. The solution was diluted with ethyl acetate and washed with water (2x) and brine, dried over MgSO4, and concentrated. The residue was chromatographed over silica gel using hexane-ethyl acetate (1:1) to give 180.6 mg of product (48%) along with 70.6 mg of 7-deoxy-10-desacetyl baccatin III (28%). Solid material was obtained by adding hexane to a hot solution of the product in ethyl acetate followed by cooling to 0° C.

ESIMS m/z 792 (M+H) IR(KBr) 3444, 1733, 1715, 1368, 1245 cm−1 1H NMR (CDCl3, 300 MHz) δ 8.13 (d, J=7.2 Hz, 2H), 7.64–7.30 (m, 8H), 6.25 (br t, J=8.4 Hz, 1H), 5.67 (d, J=6 Hz, 1H), 5.40 (d, J=9.3 Hz, 1H), 5.29 (br d, 1H), 5.20 (s, 1H), 4.94 (d, J=11 Hz, 1H), 4.61 (m, 1H), 4.33 (d, J=8.4 Hz, 1H), 4.24 (d, J=8.4 Hz, 1H), 4.19 (s, 1H), 3.83 (d, J=7.2 Hz, 1H), 3.29 (br d, 1H), 2.39 (s, 3H), 2.34–1.91 (m, 5H), 1.85 (s, 3H), 1.82 (s, 3H), 1.69 (s, 1H), 1.54 (m, 1H), 1.33 (s, 9H), 1.24 (s, 3H), 1.10 (s, 3H). Anal. Calcd for C,43H, 53NO,13: C, 65.22; H, 6.75; N, 1.77. Found: C, 64.94; H, 6.92, N, 1.45.

EXAMPLE 21

General Procedure for use in Examples 22–26

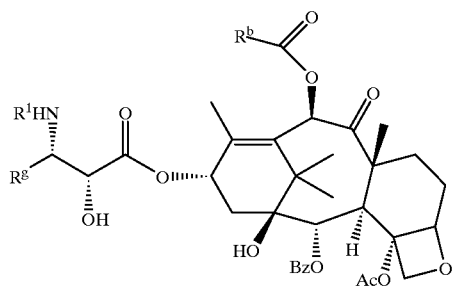

General procedure for C-10 Acylation of 2'-O-t-Butyldimethylsilyl-10-Desacetyl-7-Deoxy paclitaxel (Used for examples 22–26). 2'-O-t-Butyldimethylsilyl 10-Desacetyl-7-Deoxy paclitaxel (0.33 mmol) was dissolved in 6 mL of THF under N2. After the solution was cooled to −40° C., LiHMDS (0.40 mL, 0.4 mmol) was added to solution and stirred for 15 min before acyl chloride (0.4 mmoL) was added to the solution. The reaction mixture was warmed to 0° C. after 30 min and then stirred for another 30 min. The reaction mixture was diluted with CH2Cl2 and washed with NH4Cl. The solution was dried over MgSO4, concentrated and chromatographed over silica gel using hexane/ethyl acetate to give the 10-acylated product.

The 10-acylated product (0.22 mmol) was dissolved in THF and triethylamine trihydrofluoride (60 μL, 0.37 mmol) was added to solution. The reaction was stirred overnight at room temperature. The reaction solution was diluted with ethyl acetate and washed with saturated sodium bicarbonate solution and brine solution and dried over MgSO4. The concentrated residue was chromatographed over silica gel using hexane/ethyl acetate to give the product.

EXAMPLE 22

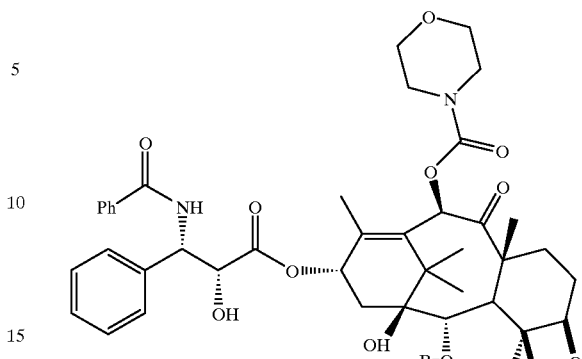

10-Morpholinoyl-7-deoxy paclitaxel. (lc)

Prepared as described by the general procedure in 69% yield,

ESIMS m/z 907 (M−H) IR (KBr) 3439, 1731, 1708, 1273, 1242, 1111 cm−1 1H NMR (300 MHz, CDCl3) δ 8.17 (d, J=7.9 Hz, 2H), 7.74 (d, J=7.9 Hz, 2H), 7.33–7.65 (m, 11H), 6.97 (d, J=8.9 Hz, 1H), 6.42 (s, 1H), 6.23 (t, J=9.4 Hz, 1H), 5.81 (dd, J=8.9, 2.4 Hz, 1H), 5.68 (d, J=7.4 Hz, 1H), 4.94 (d, J=6.8 Hz, 1H), 4.80 (m, 1H), 4.33 (d, J=8.3 Hz, 1H), 4.24 (d, J=8.6 Hz, 1H), 3.77 (brs, 9H), 3.49 (d, J=5.1 Hz, 1H), 2.45 (m, 1H), 2.41 (s, 3H), 2.26 (m, 2H), 2.12 (m, 1H), 1.94 (m, 1H), 1.86 (s, 3H), 1.78 (s, 1H), 1.76 (s, 3H), 1.62 (m, 1H), 1.21 (s, 3H), 1.14 (s, 3H). Anal Calcd for C,50H,56N,2O,14: C, 66.07; H, 6.21; N, 3.08. Found: C, 66.06; H, 6.27; N, 2.97.

EXAMPLE 23

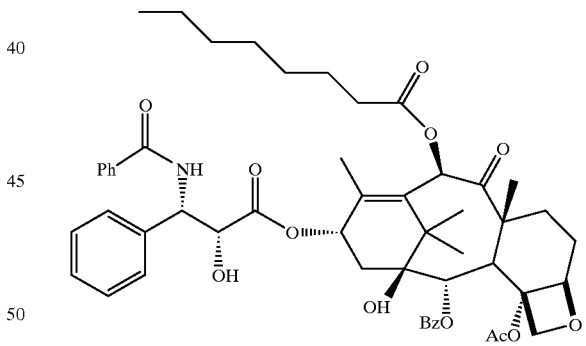

10-Octanoyl-7-deoxy paclitaxel. (ld)

Prepared as described by the general procedure in 76% yield.

ESIMS m/z 922 (M+H) IR (KBr) 3440, 1734, 1716, 1270, 1245, 1107, 1068 cm−1 1H NMR (300 MHz, CDCl3) δ 8.17 (d, J=7.9 Hz, 2H), 7.74 (d, J=7.9 Hz, 2H), 7.33–7.65 (m, 11H), 6.97 (d, J=8.9 Hz, 1H), 6.45 (s, 1H), 6.23 (t, J=7.7 Hz, 1H), 5.81 (dd, J=8.9, 2.5 Hz, 1H), 5.68 (d, J=7.3 Hz, 1H), 4.94 (d, J=8.1 Hz, 1H), 4.79 (m, 1H), 4.32 (d, J=8.4 Hz, 1H), 4.24 (d, J=8.5 Hz, 1H), 3.78 (d, J=7.3 Hz, 1H), 3.49 (d, J=5.0 Hz, 1H), 2.49 (m, 3H), 2.41 (s, 3H), 2.24 (m, 2H), 2.11 (m, 1H), 1.96 (m, 1H), 1.81 (s, 3H), 1.76 (s, 3H), 1.69 (m, 1H), 1.60 (m, 1H), 1.30 (br s, 10H), 1.22 (s, 3H), 1.15 (s, 3H), 0.89 (m, 3H). Anal Calcd for C,53H,63NO,13: C, 69.04; H, 6.89; N, 1.52. Found: C, 68.94; H, 6.93; N, 1.47.

EXAMPLE 24

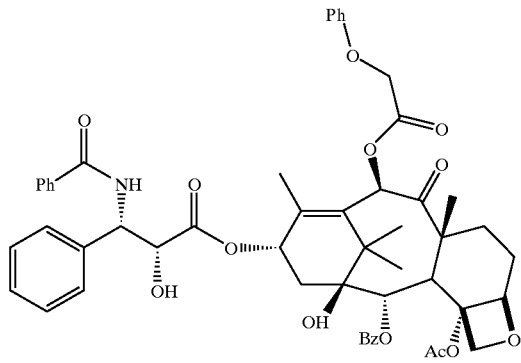

10-Phenoxyacetyl-7-deoxy paclitaxel. (1e)

Prepared as described by the genera: procedure in 64% yield.

ESIMS m/z 930 (M+H) IR (KBr) 3431, 1732, 1715, 1270, 1245, 1174, 1068 cm−1 1H NMR (300 MHz, CDCl3) δ 8.16 (d, J=7.8 Hz, 2H), 7.74 (d, J=7.9 Hz, 2H), 7.28–7.65 (m, 13H), 6.96–7.03 (m, 4H), 6.52 (s, 1H), 6.23 (t, J=18.8 Hz, 1H), 5.80 (dd, J=8.9. 2.5 Hz, 1H), 5.66 (d, J=7.3 Hz, 1H), 4.92 (d, J=8.1 Hz, 1H), 4.84 (d, J=1.4 Hz, 2H), 4.79 (m, 1H), 4.32 (d, J=8.4 Hz, 1H), 4.23 (d, J=8.3 Hz, 1H), 3.75 (d, J=7.2 Hz, 1H), 3.50 (d, J=5.1 Hz, 1H), 2.41 (s, 3H), 2.36 (m, 1H), 2.24 (m, 2H), 2.08 (m, 1H), 1.96 (m, 1H), 1.81 (s, 3H), 1.76 (s, 3H), 1.58 (m, 2H), 1.13 (s, 3H), 2.04 (s, 3H). Anal Calcd for C,53H,55NO,14: C, 68.45; H, 5.96; N, 1.51. Found: C, 68.45; H, 5.96; N, 1.46.

EXAMPLE 25

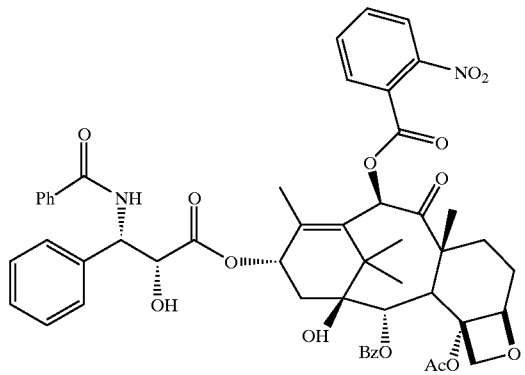

10-(2-Nitro)benzoyl-7-deoxy paclitaxel. (1f)

Prepared as described by the general procedure in 78% yield.

ESIMS m/z 945 (M+H) IR (KBr) 3425, 1730, 1716, 1270, 1245, 1159, 1108, 1068 cm−1 1H NMR (300 MHz, CDCl3) δ 8.18 (d, J=7.8 Hz, 2H), 7.94–8.01 (m, 2H), 7.34–7.78 (m, 15H), 7.01 (d, J=9.0 Hz, 1H), 6.68 (s, 1H), 6.27 (t, J=8.1 Hz, 1H), 5.82 (dd, J=9.0, 2.6 Hz, 1H), 5.69 (d, J=7.3 Hz, 1H), 4.95 (d, J=9.3 Hz, 1H), 4.82 (m, 1H), 4.34 (d, J=8.5 Hz, 1H), 4.26 (d, J=8.4 Hz, 1H), 3.81 (d, J=7.3 Hz, 1H), 3.48 (d, J=5.2 Hz, 1H), 2.45 (m, 1H), 2.43 (s, 3H), 2.19–2.32 (m, 3H), 1.99 (m, 1H), 1.91 (s, 3H), 1.84 (s, 1H), 1.79 (s, 3H), 1.66 (m, 1H), 1.21 (s, 3H), 1.11 (s, 3H). Anal Calcd for C,52H,52N,2O,15: C, 66.09; H, 5.55; N, 2.96. Found: C, 65.89; H, 5.64; N, 2.88.

EXAMPLE 26

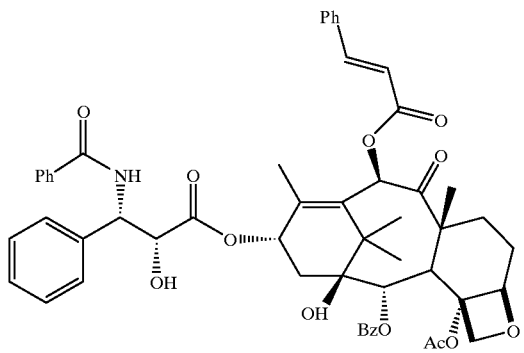

10-Cinnamoyl-7-deoxy paclitaxel. (1g)

Prepared as described by the general procedure in 82% yield

ESIMS m/z 926 (M+H) IR (KBr) 3424, 1734, 1716, 1536, 1281, 1109, 1067 cm−1 1H NMR (300 MHz, CDCl3) δ 8.18 (d, J=7.8 Hz, 2H), 7.80 (s, 1H), 7.74 (d, J=6.9 Hz, 2H), 7.33–7.65 (m, 16H), 7.00 (d, J=8.9 Hz, 1H), 6.59 (s, 1H), 6.54 (s, 1H), 6.25 (t, J=8.0 Hz, 1H), 5.81 (dd, J=8.9, 2.4 Hz, 1H), 5.71 (d, H=7.4 Hz, 1H), 4.96 (d, J=9.4 Hz, 1H), 4.81 (m, 1H), 4.34 (d, J=8.4 Hz, 1H), 4.26 (d, 8.7 Hz, 1H), 3.82 (d, J=7.3 Hz, 1H), 3.50 (d, J=5.1 Hz, 1H), 2.47 (m, 1H), 2.42 (s, 3H), 2.28 (m, 2H), 2.17 (m, 1H), 1.99 (m, 1H), 1.85 (s, 3H), 1.65 (m, 1H), 1.27 (s, 3H), 1.24 (s, 3H). Anal Calcd for C,54H,55NO,13: C, 70.04; H, 5.99; N, 1.51. Found: C, 69.89; H, 6.01; N, 1.43.

EXAMPLE 27

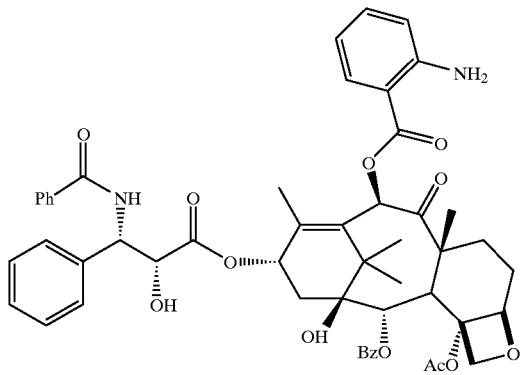

10-(2-amino)benzoyl-7-deoxy paclitaxel. (1h) To a solution of 10-(2-nitro)benzoyl-7-deoxy paclitaxel in ethanol (12 mL) was added acetic acid (0.6 mL) and 10%Pd-C (15 mg, catalytic) The reaction was stirred overnight under atmospheric pressure of nitrogen. The reaction mixture was filtered through a Celite plug and the concentrated residue was chromatographed over hexane/ethyl acetate (1:1) to give the product (97 mg, 65% yield) as a white amorphous solid.

IR (KBr) 3381, 1731, 1718, 1681, 1236, 1108, 1069 cm−1 1H NMR (300 MHz, CDCl3) δ 8.18 (d, J=7.8 Hz, 2H), 7.94

(dd, J=8.0, 1.5 Hz, 1H), 7.74 d, J=7.8 Hz, 2H), 7.33–7.65 (m, 12H), 7.01 (d, J=8.9 Hz, 1H), 6.70 (d, J=8.5 Hz, 1H), 6.66 (s, 1H), 6.64 (t, J=7.2 Hz, 1H), 6.23 (t, J=8.8 Hz, 1H), 5,81 (dd, J=8.9, 2.5 Hz, 1H), 5.73 (d, J=7.3 Hz, 1H), 4.96 (d, J=8.0 Hz, 1H), 4.80 (m, 1H), 4.34 (d, J=8.4 Hz, 1H), 4.26 (d, J=8.4 Hz, 1H), 3.85 (d, J=7.3 Hz, 1H), 3.49 (d, J=5.2 Hz, 1H), 3.25 (m, 2H), 2.48 (m, 1H), 2.43 (s, 3H), 2.17–2.33 (m, 3H), 2.23 (m, 1H), 1.85 (s, 3H), 1.78 (s, 3H), 1.66 (m, 2H), 1.33 (m, 3H), 1.29 (s, 3H).

BIOLOGICAL DATA

Cytotoxicity

The 7-deoxy taxane derivatives possessed cytoxicity in vitro against human colon carcinoma cells HCT-116. Cytoxicity was assessed in HCT-116 human colon carcinoma cells by either using an XTT or MTS procedure.

XTT

Cytotoxicity was assessed in HCT-116 human colon carcinoma cells by XTT (2,3-bis(2-methoxy-4-nitro-5-sulfpphenyl)-5-[(phenylamino)carbonyl]2H-tetrazolium hydroxide) assay as reported in D. A. Scudiero, et al., "Evaluation of soluble tetrazolium/formazan assay for cell growth and drug sensitivity in culture using human and other tumor cell lines," Cancer Res. 48:4827–4833, 1988. Cells were plated at 4000 cells/well in 96 well microtiter plates and 24 hours later drugs were added and serial diluted. The cells were incubated at 37° C. for 72 hours at which time the tetrazolium dye, XTT, was added. A dehydrogenase enzyme in live cells reduces the XTT to a form that absorbs light at 450 nm which can be quantitated spectrophotometrically. The greater the absorbance, the greater the number of live cells. The results are expressed as an IC50, which is the drug concentration required to inhibit cell proliferation (i.e., absorbance at 450 nm) to 50% of that of untreated control cells. The IC50 values for representative compounds evaluated in this assay are given in Table II.

Cytoxicity was assessed in HCT-116 human colon carcinoma cells by MTS (3-(4,5-dimethylthiazol-2-yl)-5-(3-carboxymethoxyphenyl)-2-(4-sulphenyl)-2H-tetrazolium, inner salt) assay as reported in T. L. Riss, et. al., "Comparison of MTT, XTT, and a novel tetrazolium compound MTS for in vitro proliferation and chemosensitivity assays." Mol. Biol. Cell 3 (Suppl.):184a, 1992. Cells were plated at 4,000 cell/well in 96 well microtiter plates and 24 hours later drugs were added and serial diluted. The cells were incubated at 37° form 72 hours at which time the tetrazolium dye, MTS at 333 µg/ml (final concentration), in combination with the electron coupling agent phenazine methosulfate at 25 µM (final concentration) was added. A dehydrogenase enzyme in live cells reduces the MTS to a form that absorbs light at 492 nM which can be quantitated spectrophotometrically. The greater the absorbance the greater the number of live cells. The results are expressed as an IC50, which is the drug concentration required to inhibit cell proliferation (i.e. absorbance at 450 nM) to 50% of that of untreated control cells. The IC50 values for compounds evaluated in this assay are evaluated in Table I.

TABLE 1

| Compound | Cytotoxicity IC50 (µM) | Assay Procedure |
| --- | --- | --- |
| Ia | 0.00430 | MTS |
| Ib | 0.00085 | MTS |
| Ic | 0.00149 | XTT |
| Id | 0.09819 | XTT |
| Ie | 0.00809 | XTT |
| If | 0.01327 | XTT |
| Ig | 0.02835 | XTT |
| Ih | 0.10155 | XTT |

Another aspect of the instant invention concerns a method for inhibiting human and/or other mammalian tumors which comprises administering to a tumor bearing host an antitumor effective amount of a compound of formula I.

The materials and methods utilized for the in vivo antitumor testing of our oral taxanes are summarized below:

Materials

Animals. Conventional or athymic ("nude") mice, and nude rats, were implanted subcutaneously (sc) with tumor brei or fragments. Murine tumor were implanted in conventional mice, human tumors were implanted into nude mice or rats.

Tumors. A variety of tumors have been utilized but not all of them have necessarily been used to evaluate each and every taxane. The tumors utilized most often included the murine lung carcinoma, M109, the murine mammary carcinoma, MAM 16/C, the human ovarian carcinoma. A2780, the human colon tumors, HCT-116 and HCT-116/pk.

Methods

Treatments are initiated at differing times post-implantation depending upon the desired stringency of the test system; in general, the greater the delay post-tumor implantation, the larger the tumors at the start of therapy. Typically, treatments were begun in the M109 tumor model on Day 4 post-tumor implant, Day 7 in the MAM 16/C tumor model, and when tumors were between 100 and 500 mg in size (typically Day 7 to Day 12 post-tumor implant) for each of the human tumor xenograft models (e.g., A2780, HCT-116 and HCT-116/pk). Group sizes were typically 8 per treatment and control groups in mouse experiments and 7 per treatment and control groups in rat experiments.

Treatments for taxanes administered orally (po) were done by gavage using a vehicle consisting of 10% ethanol +10% Cremophor EL+80% water. The volume of liquid administered was 0.01 ml per gram of body weight for mice, and 0.005 ml per gram of body weight for rats. A typical mouse experiment would involve the evaluation of each test compound at three different dose levels, but only one to three test groups per compound were included in rat experiments. In every experiment, intravenously (iv) administered paclitaxel was included as a reference drug.

Paclitaxel was administered iv on treatment schedules and doses established from experience as being optimal, or near optimal, for the particular tumor, tumor staging, and host animal under study. It was given once daily, for five consecutive daily treatments (i.e., qdx5), when evaluated in the M109 and MAM 16/C tumor models, once daily every other day for five treatments (i.e., q2dx5) when administered to mice bearing human tumors, and once daily every other or every fourth day for five or three treatments, respectively (i.e., q2dx5 or q4dx3), to rats.

Orally administered taxanes were evaluated on the same treatment schedules just described for iv administered paclitaxel, plus other treatment schedules such as daily for nine days, or every eight days for two treatments.

Antitumor activity was assessed by determining the size of tumors in all treated and control experimental animals over time. Each animal was individually identified and the growth of the tumor implanted into each animal was measured once or twice weekly using a calipers. The difference in median time for tumors in treated (T) and control (C) groups to reach a predetermined size (e.g., 500 or 1,000 milligrams) was calculated, and assessments of absolute and relative antitumor effects (e.g., between compounds) were made on the basis of the delays in time to reach predetermined tumor target sizes. Animals with tumors of 35 mg or less at the termination of an experiment were termed "cures". Experiments were terminated typically after a period of time had elapsed post-treatment that was at least 10 times the tumor volume doubling time (TVDT) of the median tumor growth in control animals as assessed prior to their reaching the predetermined tumor target size in each experiment. Activity in a test group was defined as having caused a delay in tumor growth (median time to reach tumor target size) relative to the concomitant control tumor growth (i.e. T-C) of 3.32 times the TVDT. Activity was expressed in log cell kill which was equal to (T-C)/(TVDT×3.32). Toxicity was determined by measuring the average body weight of all animals in an experiment prior to, and soon after, any treatments in the experiment. Additionally, animals were considered to have died due to treatment-induced injury if they died prior to any deaths in the control group with tumors smaller than target size. No results of therapy, nor any declaration of activity, was used or made for a particular treatment group if more than one animal in that group died in a manner characterized as treatment-induced.

| Compound | Tumor Model | IV Activity in LCK | iv Dose* in mg/kg Per Injection | PO Activity in LCK | PO dose* in mg/kg | Optimal Activity of iv Paclitaxel |
|---|---|---|---|---|---|---|
| Ia | M109 | 1.4 | 13 | No Result$^a$ | No Result$^a$ | 0.7 |
| Ib | M109 | 0.7 | 20 | 0.7 | 40 | 0.7 |
|  | A2780 | Not tested | Not tested | >7 (1/8)** | 85 | 5.9 |

*The dose given is for a single administration. For the total number of doses administered and the dosing regimen for each specific tumor model see the details in the text.
**One of eight tested mice was cured
$^a$In the initial experiment, doses which were higher than the maximum tolerated dose and thus toxic were inadvertently chosen. Additional experiments at a lower dose will gauge the oral potential of the compound.

As can be seen from the in vivo data, iv compound Ia had surprising activity compared to concomitantly evaluated iv paclitaxel in the treatment of the scM109 tumors in vivo. It is not clear that the dose of 13 mg/kg was the maximum tolerated dose so a higher dose may be even more efficacious. The activity given for paclitaxel is under conditions known to give the maximized result for paclitaxel. Also, compound Ib is equiactive to paclitaxel when given by the iv route in the M109 model but unlike paclitaxel or docetaxel (the active ingredient of the other commercial taxane) this Ib is active orally in this model. In the A2780 model, the unusual oral activity of compound Ib is confirmed. In addition. it is equallyactive if not better than the optimal activity observed for concomitantly evaluated iv paclitaxel.

For treating a variety of tumors, the compound of formula I of the present invention may be used in a manner similar to that of paclitaxel, e.g. see Physician's Desk Reference, 49th Edition, Medical Economics, p 682, 1995. The dosage, mode and schedule of administration for the compound of this invention are not particularly restricted; an oncologist skilled in the art of cancer treatment will be able to ascertain, without undue experimentation, an appropriate treatment protocol for administering the compound of the present invention. Thus the compound of formula I may be administered via any suitable route of administration, parenterally or orally. Parenteral administration includes intravenous, intraperitoneal, intramuscular, and subcutaneous administration.

The doses utilized to implement the methods in accordance with the invention are the ones that make it possible to administer prophylactic treatment or to evoke a maximal therapeutic response. The doses vary, depending on the type of administration, the particular product selected, and the personal characteristics of the subject to be treated. In general, the doses are the ones that are therapeutically effective for the treatment of disorders caused by abnormal cell proliferation. The products in accordance with the invention can be administered as often as necessary in order to obtain the desired therapeutic effect. Some patients may respond rapidly to relatively high or low doses, and then require mild maintenance or no maintenance dose at all. Via the iv route, the dosage may be, for example, in the range of about 20 to about 500 mgm2 over 1 to 100 hours. Via the oral route, the dosage may be in the range of 5–1000 mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of compound of formula I in combination with one or more pharmaceutically acceptable carriers, excipients, diluents or adjuvants. The compositions can be prepared in accordance with conventional methods. Examples of formulating paclitaxel or derivatives thereof may be found in, for example, U.S. Pat. Nos. 4,960,790 and 4,814,470, and such examples may be followed to formulate the compound of this invention. Additional examples of paclitaxel formulations are found in the general references cited earlier in the background art. For example, compound of formula I may be formulated in the form of tablets, pills, powder mixtures, capsules, injectables, solutions, suppositories, emulsions, dispersions, food premix, and in other suitable forms. It may also be manufactured in the form of sterile solid compositions, for example, freeze dried and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use for parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose. poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

What is claimed is:

1. A compound of formula I

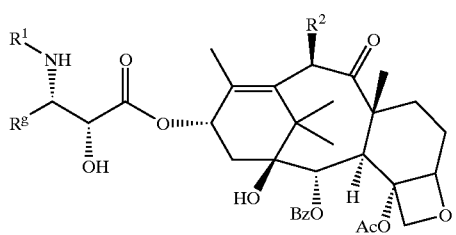

I wherein $R^1$ is —$COR^z$ in which $R^z$ is RO—, R, or heteroaryl, with the proviso that $R^z$ must be heteroaryl unless either (1) $R^g$ is $R^k$ or $R^2$ is —$OCOR^b$, or (2) $R^g$ is $R^k$ and $R^2$ is —$OC(O)R^b$;

$R^g$ is $C_{3-6}$ alkyl, $C_{3-6}$ alkenyl, $C_{3-6}$ alkynyl $C_{3-6}$ cycloalkyl, $R^k$, or a radical of the formula —W—$R^x$ in which W is a bond, or —$(CH_2)_t$—, in which t is one or 2;

$R^x$ is phenyl or heteroaryl, and futhermore $R^x$ can be optionally substituted with one to three same or different $C_{1-6}$ alkyl, $C_{1-6}$ alkoxy, halogen or —$CF_3$ groups;

$R^k$ is a radical of the formula —W—$R^s$ in which W is a bond, or —$(CH_2)_t$—, in which t is one or 2; and $R^s$ is phenyl substituted with hydroxy;

$R^2$ is —OCOR, H, OH, —OR, —$OSO_2R$, —$OCONR^oR$, —OCONHR, —$OCOO(CH_2)_tR$, —OCOOR, or —$OCOR^b$;

R and $R^o$ are independently $C_{1-6}$ alkyl, $C_{3-6}$ cycloalkyl, benzyl, or phenyl, optionally substituted with either one hydroxy group or with one to three same or different $C_{1-6}$ alkyl, $C_{1-6}$ alkoxy, halogen or —$CF_3$ groups; and $R^b$ is -morpholino, -nheptyl, —$CH_2OPh$, —(2-nitrophenyl), —CH=CHPhenyl or —(2-aminophenyl).

2. A compound of claim 1 in which $R^2$ is —$OCOR^b$; and $R^g$ is phenyl, 2-furyl, 2-thienyl $C_{3-6}$ alkyl, $C_{3-6}$ alkenyl, $C_{3-6}$ cycloalkyl or $R^k$, provided t is 0 when $R^g$ is $R^k$ and $R^s$ is parahydroxyphenyl; and $R^z$ is $C_{1-6}$alkyloxy, phenyl, or heteroaryl.

3. A compound of claim 2 in which $R^g$ is phenyl; and $R^z$ is tBuO—, phenyl, or 2-Furyl.

4. A compound of claim 1 in which $R^2$ is —OCOR, H, OH, —OR, or —OCOOR; and $R^g$ is $R^k$; and $R^z$ is $C_{1-6}$alkyloxy, phenyl, or heteroaryl.

5. A compound of claim 4 in which $R^2$ is hydrogen, hydroxy, or acetyloxy; $R^g$ is $R^k$; and R1 is $C_{3-6}$alkyloxycarbonyl, benzoyl, or heteroaryl.

6. A compound of claim 5 in which $R^g$ is parahydroxyphenyl.

7. The compound of claim 6 that is N-debenzoyl-N-t-butoxycarbonyl-3'-dephenyl-3'-(parahydroxyphenyl)-7-deoxypaclitaxel.

8. A compound of claim 1 in which $R^z$ is heteroaryl.

9. A compound of claim 8 in which $R^2$ is hydrogen, hydroxy or acetyloxy; and $R^g$ is phenyl, 2-furyl, 2-thienyl $C_{3-6}$ alkyl, $C_{3-6}$ alkenyl, $C_{3-6}$ cycloalkyl,or $R^k$ where t is 0 and $R^s$ is parahydroxyphenyl.

10. A compound of claim 9 in which $R^z$ is 2-furyl, 3-furyl, 2-thienyl, or 3-thienyl.

11. A compound of claim 10 in which $R^2$ is acetyloxy; and $R^g$ is phenyl, $C_{3-6}$ alkyl, or $C_{3-6}$ cycloalkyl.

12. The compound of claim 11 that is N-debenzoyl-N-(2-furyl)carbonyl-7-deoxypaclitaxel.

13. The compound of claim 11 that is N-debenzoyl-N-(3-furyl)carbonyl-7-deoxypaclitaxel.

14. The compound of claim 11 that is N-debenzoyl-N-(2-thienyl)carbonyl-7-deoxypaclitaxel.

15. A pharmaceutical formulation which comprises as an active ingredient a compound as claimed in any one of claims 1 to 14, associated with one or more pharmaceutically acceptable carriers, excipients or diluents therefor.

16. A method for treating mammalian tumors which comprises administering to a mammal a tumor sensitive amount of a compound as claimed in any one of claims 1 to 14.

17. A method for treating mammalian tumors which comprises orally administering to a mammal a tumor sensitive amount of a compound of claim 8.

18. A method for the preparation of 7-deoxy taxanes, baccatins, and synthetic intermediates which comprises hydrogenation of a 6,7-olefin-containing taxane or baccatin.

* * * * *